US011406971B2

(12) United States Patent
Luz Minguez et al.

(10) Patent No.: US 11,406,971 B2
(45) Date of Patent: Aug. 9, 2022

(54) METHOD OF MAKING CONFINED NANOCATALYSTS WITHIN MESOPOROUS MATERIALS AND USES THEREOF

(71) Applicant: RESEARCH TRIANGLE INSTITUTE, Research Triangle Park, NC (US)

(72) Inventors: Ignacio Luz Minguez, Durham, NC (US); Mustapha Soukri, Cary, NC (US); Marty Lail, Raleigh, NC (US); John R Carpenter, Apex, NC (US); Sameer Parvathikar, Raleigh, NC (US); Michael Carpenter, Raleigh, NC (US)

(73) Assignee: Research Triangle Institute, Research Triangle Park, NC (US)

(*) Notice: Subject to any disclaimer, the term of this patent is extended or adjusted under 35 U.S.C. 154(b) by 0 days.

(21) Appl. No.: 17/041,944

(22) PCT Filed: Mar. 26, 2019

(86) PCT No.: PCT/US2019/023989
§ 371 (c)(1),
(2) Date: Sep. 25, 2020

(87) PCT Pub. No.: WO2019/191034
PCT Pub. Date: Oct. 3, 2019

(65) Prior Publication Data
US 2021/0008529 A1   Jan. 14, 2021

Related U.S. Application Data

(60) Provisional application No. 62/647,949, filed on Mar. 26, 2018.

(51) Int. Cl.
*B01J 29/035* (2006.01)
*C07F 15/00* (2006.01)
(Continued)

(52) U.S. Cl.
CPC .............. *B01J 29/035* (2013.01); *C07F 1/12* (2013.01); *C07F 5/00* (2013.01); *C07F 5/061* (2013.01);
(Continued)

(58) Field of Classification Search
CPC .............. B01J 29/0308; B01J 29/0352; B01J 29/0354; B01J 29/0356; B01J 29/0358; B01J 37/0209; B01J 37/16; B01J 37/18
See application file for complete search history.

(56) References Cited

U.S. PATENT DOCUMENTS 9,566,575 B2    2/2017   Bohringer et al.
2009/0263621 A1  10/2009   Chang et al.
(Continued)

FOREIGN PATENT DOCUMENTS

CN    105056895 A    11/2015
CN    107774331 B    3/2018
(Continued)

OTHER PUBLICATIONS

Cirujano et al, "Boosting the Catalytic Performance of Metal-Organic Frameworks for Steroid Transformations by Confinement within a Mesoporous Scaffold", Ang. Chem. International Ed, vol. 56, Iss 43, 13302-13306 (Sep. 2017) (Year: 2017).*

(Continued)

*Primary Examiner* — Colin W. Slifka
(74) *Attorney, Agent, or Firm* — Olive Law Group PLLC; Nathan P. Letts

(57) ABSTRACT

The present disclosure provides methods of making confined nanocatalysts within mesoporous materials (MPMs). The methods utilize solid state growth of nanocrystalline metal organic frameworks (MOFs) followed by controlled transformation to generate nanocatalysts in situ within the mesoporous material. The disclosure also provides applications (Continued)

Figure 1:
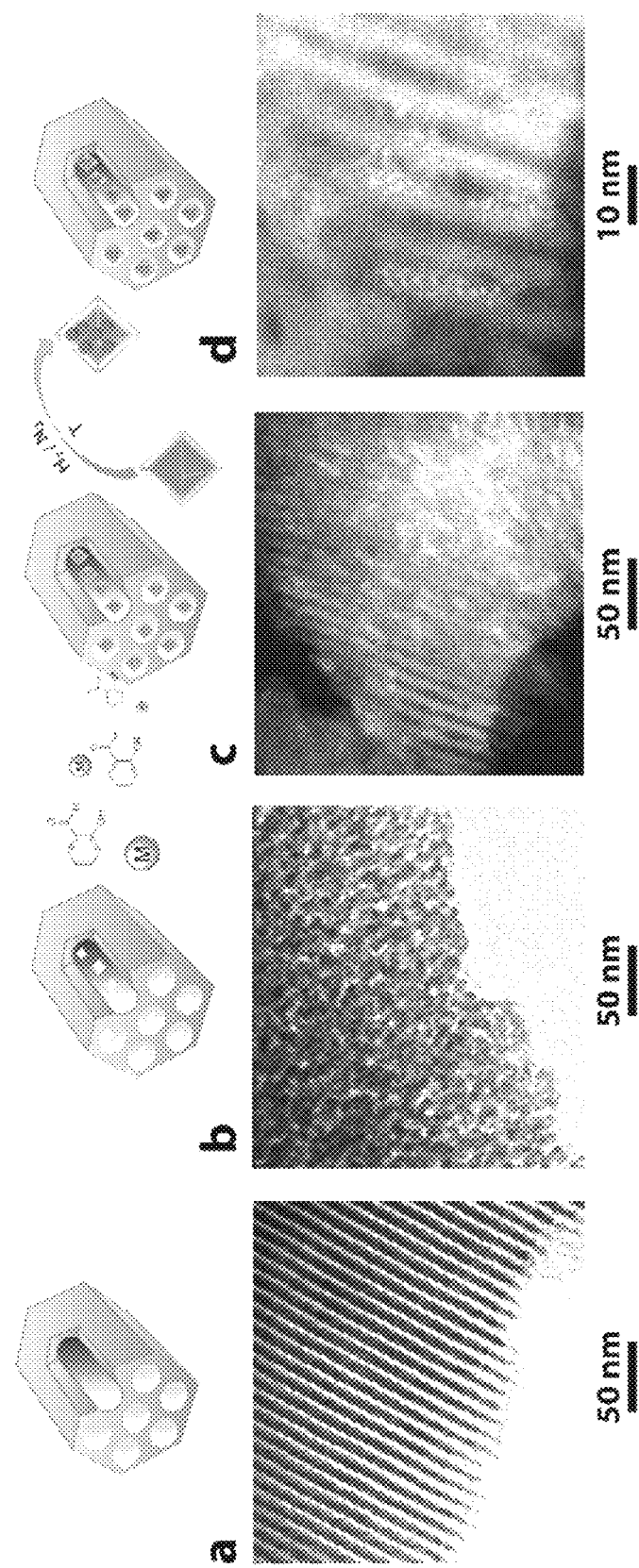

of the nanocatalysts to a wide variety of fields including, but not limited to, liquid organic hydrogen carriers, synthetic liquid fuel preparation, and nitrogen fixation.

24 Claims, 8 Drawing Sheets

(51) Int. Cl.
    *C07F 15/04* (2006.01)
    *C07F 9/00* (2006.01)
    *C07F 11/00* (2006.01)
    *C07F 1/12* (2006.01)
    *C07F 7/28* (2006.01)
    *C07F 15/02* (2006.01)
    *C07F 5/00* (2006.01)
    *C07F 7/00* (2006.01)
    *C07F 15/06* (2006.01)
    *C07F 5/06* (2006.01)

(52) U.S. Cl.
    CPC ............... *C07F 7/00* (2013.01); *C07F 7/28* (2013.01); *C07F 9/00* (2013.01); *C07F 11/00* (2013.01); *C07F 15/00* (2013.01); *C07F 15/006* (2013.01); *C07F 15/0033* (2013.01); *C07F 15/0046* (2013.01); *C07F 15/0073* (2013.01); *C07F 15/02* (2013.01); *C07F 15/04* (2013.01); *C07F 15/06* (2013.01)

(56) References Cited

U.S. PATENT DOCUMENTS

| | | | |
|---|---|---|---|
| 2011/0118490 | A1 | 5/2011 | Hwang et al. |
| 2011/0144365 | A1 | 6/2011 | Park et al. |
| 2012/0152845 | A1 | 6/2012 | Levan et al. |
| 2013/0273461 | A1 | 10/2013 | Liu et al. |
| 2014/0099571 | A1 | 4/2014 | Proietti et al. |

FOREIGN PATENT DOCUMENTS

| | | |
|---|---|---|
| EP | 2341031 A1 | 7/2011 |
| KR | 20200127038 A | 11/2020 |
| WO | 2018031733 A8 | 2/2018 |

OTHER PUBLICATIONS

Luz et al,"Confining Metal-Organic Framework nanocrystals within mesoporous materials: a general approach via solid-state synthesis", Chem. Mater. (Aug. 2017) 29, 9628-9638 and supplementary material. (Year: 2017).*
International Search Report from related PCT application PCT/US2019/023989 dated Aug. 9, 2019. (3 pages).
Written Opinion from related PCT application PCT/US2019/023989 dated Aug. 9, 2019. (8 pages).
Bielawa, H. et al. "The ammonia-synthesis catalyst of the next generation: Barium-promoted oxide-supported ruthenium." Angewandte Chemie-International Edition 2001, 40, 1061-1063, John Wiley & Sons, Inc., Hoboken, NJ. (3 pages).
Brazdil, J. F. "Designing Multifunctionality into Single Phase and Multiphase Metal-Oxide-Selective Propylene Ammoxidation Catalysts." Catalysts 2018, 8(3), 103, MDPI, Basel, Switzerland. (19 pages).
Cheddie, D. "Ammonia as a Hydrogen Source for Fuel Cells: A Review" in Minic, D. (Ed.) Hydrogen Energy—Challenges and Perspectives, 2012, 333-361, InTech, London. (31 pages).
Cirujano, F. G. et al. "Boosting the Catalytic Performance of Metal-Organic Frameworks for Steroid Transformations by Confinement within a Mesoporous Scaffold." Angewandte Chemie International Edition, 2017, 56, 13302-13306, John Wiley & Sons, Inc., Hoboken, NJ. (7 pages).

Couck, S. et al. "An Amine-Functionalized MIL-53 Metal-Organic Framework with Large Separation Power for CO2 and CH4." J. Am. Chem. Soc. 2009, 131(18), 6326-6327, American Chemical Society (ACS), Washington, D.C. (2 pages).
Cravillon, J. et al. "Rapid Room-Temperature Synthesis and Characterization of Nanocrystals of a Prototypical Zeolitic Imidazolate Framework." Chem. Mater. Mar. 26, 2009, 21(8), 1410-1412, American Chemical Society, Washington, D.C. with Supplement (24 pages).
Dębek, R. et al., Maria Elena Galvez, Franck Launay, Monika Motak, Teresa Grzybek & Patrick Da Costa, "Low temperature dry methane reforming over Cr, Zr and CeZr promoted Ni—Mg—Al hydrotalcite-derived catalysts." International Journal of Hydrogen Energy, 2016, 41 (27), 11616-11623, Elsevier, Amsterdam, Netherlands. (9 pages).
Deria, P. et al. "Versatile functionalization of the NU-1000 platform by solvent-assisted ligand incorporation." Chem. Commun., Feb. 24, 2014, 50(16), 1965-1968, Royal Society of Chemistry (RSC), London, UK. (5 pages).
Dietzel, P. D. C. et al. "An In Situ High-Temperature Single-Crystal Investigation of a Dehydrated Metal-Organic Framework Compound and Field-Induced Magnetization of One-Dimensional Metal-Oxygen Chains." Angew. Chem., Int. Ed. Oct. 7, 2005, 44 (39), 6354-6358, John Wiley & Sons, Inc., Hoboken, NJ. (5 pages).
Dietzel, P. D. C. et al. "Hydrogen adsorption in a nickel based coordination polymer with open metal sites in the cylindrical cavities of the desolvated frame-work." Chem. Commun. Mar. 7, 2006, 959-961, RSC, London, UK. (3 pages).
Escande, V. Eddy Petit, Laetitia Garoux, Clotilde Boulanger, and Claude Grison, "Switchable Alkene Epoxidation/Oxidative Cleavage with H2O2/NaHCO3: Efficient Heterogeneous Catalysis Derived from Biosourced Eco-Mn." ACS Sustainable Chem. Eng., 2015, 3 (11), pp. 2704-2715, ACS, Washington, D.C. (12 pages).
Farrauto, R. J. et al. "Catalytic converters: state of the art and perspectives," Catalysis Today, Jul. 29, 1999, 51(3-4), 351-360, Elsevier, Amsterdarm, Netherlands. (10 pages).
Fei, H. et al. "A robust, catalytic metal-organic framework with open 2,2-bipyridine sites." Chem. Commun. May 14, 2014, 50(37), 4810-4812, RSC, London, UK. (3 pages).
Feng, D. et al. "Zirconium-Metalloporphyrin PCN-222: Mesoporous Metal-Organic Frameworks with Ultrahigh Stability as Biomimetic Catalysts." Angew. Chem., Int. Ed. Oct. 8, 2012, 51(41), 10307-10310, John Wiley & Sons, Inc., Hoboken, NJ. (4 pages).
Ferey, G. et al. "A chromium terephthalate-based solid with unusually large pore volumes and surface area." Science, Sep. 23, 2005, 309(5743), 2040-2042, American Association for the Advancement of Science (AAAS), Washington, D.C. (4 pages).
Gomez-Gualdron, D. A. et al. "Application of Consistency Criteria to Calculate BET Areas of Micro- and Mesoporous Metal-Organic Frameworks." J. Am. Chem. Soc., Jan. 13, 2016, 138(1), 215-224, ACS, Washington, D.C. (10 pages).
Juan-Alcaniz, J. et al. "Towards acid MOFs—catalytic performance of sulfonic acid functionalized architectures." Catal. Sci. Technol. Jun. 4, 2013, 3, 2311-2318, RSC, London, UK. (8 pages).
Kandiah, M. et al. "Synthesis and Stability of Tagged UiO-66 Zr-MOFs." Chem. Ma-ter. Dec. 3, 2010, 22(24), 6632-6640, ACS, Washington, D.C. (9 pages).
Koo, W. et al., "Metal-organic framework templated synthesis of ultrasmall catalyst loaded ZnO/ZnCo2O4 hollow spheres for enhanced gas sensing properties", Scientific Reports, Mar. 22, 2017, 7 (45074), 1-10, Springer Nature Limited, Berlin, Germany. (10 pages).
Kozachuk, O. et al. "Multifunctional, Defect-Engineered Metal-Organic Frameworks with Ruthenium Centers: Sorption and Catalytic Properties." Angew. Chem., Int. Ed. Jul. 1, 2014, 53(27), 7058-7062, John Wiley & Sons, Inc., Hoboken, NJ. (5 pages).
Lee, K. J. et al. "Transformation of Metal-Organic Frameworks/Coordination Polymers into Functional Nanostructured Materials: Experimental Approaches Based on Mechanistic Insights," Accounts of Chemical Research Nov. 21, 2017, 50(11), 2684-2692, ACS, Washington, D.C. (9 pages).
Li, P. et al. "Immobilization of Metal-Organic Framework Nanocrystals for Advanced Design of Supported Nanocatalysts." ACS Applied

(56) References Cited

OTHER PUBLICATIONS

Materials & Interfaces, Oct. 24, 2016, 8, 29551-29564, ACS, Washington, D.C. with Supplement (31 pages).
Liu, L. et al. "Generation of subnanometric platinum with high stability during transformation of a 2D zeolite into 3D." Nature Materials 2017, 16, 132-138, Springer Nature Limited, Berlin, Germany. (8 pages).
Liu, Q., et al. "Using carbon dioxide as a building block in organic synthesis." Nat Commun, Jan. 20, 2015, 5933, 6, Springer Nature, Berlin. (15 pages).
Long, P. et al. "Solvent effect on the synthesis of MIL-96(Cr) and MIL-100(Cr)." Microporous Mesoporous Mater. Jul. 2011, 142(2-3), 489-493, Elsevier, Amsterdam, Netherlands. (5 pages).
Luz, I. et al., "Transformation of single MOF nanocrystals into single nanostructured catalysts within mesoporous supports: a platform for pioneer fluidized-nanoreactor hydrogen carriers", Chemical Communications, Jul. 3, 2018, 54 (61), 8462-8465, RSC, London, UK. with Supplement (24 pages).
Masoomi, M. Y. et al. "Applications of metal-organic coordination polymers as precursors for preparation of nano-materials." Coordination Chemistry Reviews, Dec. 2012, 256 (23-24), 2921-2943, Elsevier, Amsterdam, Netherlands. (23 pages).
McDonald et al. "Cooperative insertion of CO2 in diamine-appended metal-organic frameworks." Nature, Mar. 19, 2015, 519 (7543), 303-308, Springer Nature Limited, Berlin, Germany. (30 pages).
Ocampo, F. et al. "CO2 methanation over Ni-Ceria-Zirconia catalysts: effect of preparation and operating conditions." IOP Conf. Series: Materials Science and Engineering, 2011, 19, 012007, IOP Publishing, Bristol, United Kingdom. (12 pages).
Preuster, P. et al. "Liquid Organic Hydrogen Carriers (LOHCs): Toward a Hydrogen-free Hydrogen Economy." Accounts of Chemical Research, 2017, 50(1), 74-85, ACS, Washington, D.C. (12 pages).
Prieto, G. et al. "Towards stable catalysts by controlling collective properties of supported metal nanoparticles." Nature Materials 2013, 12, 34-39, Springer Nature Limited, Berlin, Germany, with Supplementary (31 pages).
Ravi, M., Marco Ranocchiari and Jeroen A. van Bokhoven Angew. "The Direct Catalytic Oxidation of Methane to Methanol—A Critical Assessment." Chem. Int. Ed. 2017, 56, 16464-16483, John Wiley & Sons, Inc., Hoboken, NJ. (20 pages).
Serre, C. et al. "Very Large Breathing Effect in the First Nanoporous Chromium(III)-Based Solids: MIL-53 or CrIII(OH)•{O2C—C6H4—CO2} {HO2C—C6H4—C02H}x-H2Oy." J. Am. Chem. Soc., Nov. 13, 2002, 124(45), 13519-13526, ACS, Washington, D.C. (8 pages).
Servalli, M.; Ranocchiari, M.; Van Bokhoven, J. A.: "Fast and high yield post-synthetic modification of metal-organic frameworks by vapor diffusion." Chemical Communications 2012, 48, 1904-1906, RSC, London, UK. (3 pages).
Tang, J. et al. "Bimetallic Metal-Organic Frameworks for Controlled Catalytic Graphitization of Nanoporous Carbons." Scientific Reports 2016, 6, 30295, Springer Nature Limited, Berlin, Germany. (8 pages).
Tsuji, Y., et al. "Ammonia synthesis over Co—Mo alloy nanoparticle catalyst prepared via sodium naphthalenide-deriven reduction." Chem. Commun., 2016, 14369-14372, 52(100), RSC, London, UK. (5 pages).
Volkringer, C. et al. "Synthesis, Single-Crystal X-ray Microdiffraction, and NMR Characterizations of the Giant Pore Metal-Organic Framework Aluminum Trimesate MIL-100." Chem. Mater. 2009, 21, 5695-5697, ACS, Washington, D.C. (3 pages).
Wei, J. et al. "Directly converting CO2 into a gasoline fuel." Nat. Commun, May 2, 2017, 8, 15174-15182, Springer Nature Limited, Berlin, Germany. (8 pages).
Wezendonk, T. A. et al. "Elucidating the Nature of Fe Species during Pyrolysis of the Fe-BTC MOF into Highly Active and Stable Fischer-Tropsch Catalysts." ACS Catalysis 2016, 6 (5), 3236-3247, ACS, Washington, D.C. (13 pages).
Zhang, X. et al. "Gold(III)—Metal Organic Framework Bridges the Gap between Homogeneous and Heterogeneous Gold Catalysts." Journal of Catalysis, Jul. 25, 2009, 265(2), 155-160, Elsevier, Amsterdam, Netherlands. (6 pages).
Zhao, D. Y. et al. "Triblock copolymer syntheses of mesoporous silica with periodic 50 to 300 angstrom pores." Science, Jan. 23, 1998, 279(5350), 548-552, AAAS, Washington, D.C. (5 pages).
International Preliminary Report on Patentability from related PCT application PCT/US2019/023989 dated Sep. 29, 2020. (9 pages).
Examination Report issued by Intellectual Property India in reference to related IN application 201917002759 dated Nov. 24, 2020 (6 pages).
Dejong, K.P. et al, The platinum rush, Porous Catalysts, Jan. 2017, 16, 7-8, Nature Materials, Springer Nature Limited, Berlin, Germany. (2 pages).
Non-Final Office Action for related U.S. Appl. No. 16/324,296 dated Feb. 10, 2021. (9 pages).
Notification of Reasons for Refusal for related Japanese application No. 2019-502086 dated Mar. 16, 2021. (3 pages).
Notification of Reasons for Refusal for related Japanese application No. 2019-502086 dated Mar. 16, 2021. English Translation (5 pages).
Foreign Non-final Office Action in related European application No. 17754960.7 dated Jun. 4, 2021. (3 pages).
Wu et al., "Facile synthesis of MOF-5 confined in SBA-15 hybrid material with enhanced hydrostability," Chemical Communications, 2013, 1223-1225, 49, Royal Society of Chemistry, London. (6 pages).
Karimi, Z., et al. "Modulated formation of metal-organic frameworks by oriented growth over mesoporous silica." J. Mater. Chem. A, 2013, 3047-3054, 1 (9), Royal Society of Chemistry (RSC), United Kingdom, and supplementary material. (10 pages).
Liu, Y., et al. "Synthesis of continuous MOF-5 membranes on porous a-alumina substrates." Microporous and Mesoporous Materials, 2009, pp. 296-301, 118 (1-3), Elsevier, Amsterdam. (6 pages).
Furtado, M. et al. "Mesoporous silica-metal organic composite: synthesis, characterization, and ammonia adsorption." J. Mater. Chem., 2011, 6698-6706, 21 (18), RSC, United Kingdom. (9 pages).
Yan, X., et al. "Facile synthesis of mesoporous MOF/silica composites." RSC Adv., 2014, 57501-57504, 4 (101), RSC, United Kingdom. (4 pages).
Sorribas, S., et al. "Synthesis and gas adsorption properties of mesoporous silica-NH2-MIL-53(Al) core-shell spheres." Microporous and Mesoporous Materials, 2016, 116-121, 225, Elsevier, Amsertdam. (6 pages).
Examination Report from European Patent Office in relation to EP application 17754960.7-1105, dated Mar. 19, 2020. (6 pages).
Yan, X., et al. "Electronic Supplementary Material (ESI)—Facile synthesis of mesoporous MOF/silica composites" RSC Adv., 2014, 4 (101), RSC, United Kingdom. (5 pages).
Corma, A. et al. 2010. "Engineering Metal Organic Frameworks for Heterogeneous Catalysis." Chem. Rev. vol. 110. pp. 4606-4655. (50 pages).
Della Rocca, Joseph et al. 2011. "Nanoscale Metal—Organic Frameworks for Biomedical Imaging and Drug Delivery." Accounts of Chemical Research. vol. 44. No. 10. pp. 957-968. (12 pages).
Doherty, Cara M. et al. 2014. "Using Functional Nano- and Microparticles for the Preparation of Metal-Organic Framework Composites with Novel Properties." Accounts of Chemical Research. vol. 47. No. 2. pp. 396-405. (10 pages).
Furukawa, Hiroyasu et al. 2013. "The Chemistry and Applications of Metal-Organic Frameworks." Science. vol. 341. p. 974 (123044) (14 pages).
Kreno, Lauren E. et al. 2012. "Metal-Organic Framework Materials as Chemical Sensors." Chem. Rev. vol. 112. pp. 1105-1125. (21 pages).
Li, Jian-Rong et al. 2012. "Metal-Organic Frameworks for Separations." Chem. Rev. vol. 112. pp. 869-932. (64 pages).
Li, Shaozhou, and Fengwei Huo. 2015. "Metal-organic framework composites: from fundamentals to applications." Nanoscale. vol. 7. pp. 7482-7501. (20 pages).

(56) References Cited

OTHER PUBLICATIONS

Li, Zheng and Hua Chun Zeng. 2014. "Armored MOFs: enforcing soft microporous MOF nanocrystals with hard mesoporous silica." J. Am. Chem. Soc. (22 pages).

Metal-organic framework. Wikipedia. Accessed Jul. 24, 2017. (24 pages).

Silva, Patricia, et al. 2015. "Multifunctional metal-organic frameworks: from academia to industrial applications." Chem. Soc. Review. vol. 44. pp. 6774-6803. (30 pages).

Stavila, V. et al. 2014. "MOF-based electronic and opto-electronic devices." Chem. Soc. Rev. vol. 43. pp. 5994-6010. (17 pages).

Sumida, Kenji et al. "Carbon Dioxide Capture in Metal-Organic Frameworks." 2012. Journal American Chemical Society vol. 112. pp. 724-781. (58 pages).

Zhan, Guowu, and Zeng, Hua Chun. 2016. "Integrated nanocatalysts with mesoporous silica/silicate and microporous MOF materials." pp. 1-12. (12 pages).

International Preliminary Report on Patentability issued in related PCT Application No. PCT/US2017/046231 dated Feb. 12, 2019. (12 pages).

Foreign Office Action for counterpart Japanese patent application 2019-502086 filed Nov. 8, 2016, dated Mar. 16, 2021. (3 pages).

Luz et al., Understanding the Formation Mechanism of metal Nanocrystal@MOF-74 Hybrids, Chemistry of Materials, May 24, 2016, 3839-3849, 28, American Chemical Society, Washington, D.C. (11 pages).

Gandara et al. High Methane Storage Capacity in Aluminum Metal-Organic Frameworks, Journal of the American Chemical Society, 2014, 5271-5274, 136, American Chemical Society, Washington, D.C. (4 pages).

Hung et al., Room-Temperature Formation of Hollow Cu2O Nanoparticles, Advanced Materials, 2010, 1910-1914, 22, Wiley-VCH, Weinheim. (5 pages).

Kim et al. Water harvesting from air with metal-organic frameworks powered by natural sunlight, Renewable Resources Repot, Apr. 28, 2017, 356, 430-434, Science, Washington, D.C. (5 pages).

Office Action in related Chinese Application No. 2017800480299 dated Sep. 16, 2021 (13 pages).

Office Action in related Korean Application No. 10-2019-7005796 dated Sep. 30, 2021. (33 pages).

Chakraborty, A, et al. "Mg-MOF-74@SBA-15 hybrids: Synthesis, characterization, and adsorption properties". APL Materials 2, 124107 (2014)(8 pages).

Kondo, A., et al. New insight into mesoporous silica for nano metal-organic framework. J Colloid Interface Sco, 384 (1), 110-115 (2012).

Examination Report in related Australian application No. 2017311400 dated Jul. 29, 2021. (14 pages).

Examination Report No. 2 for associated Australian patent application No. 2017311400 dated Dec. 1, 2021 (3 pages).

Extended European Search Report dated Nov. 19, 2021 for associated European Application No. 19776162.0 (10 pages).

Luz, Ignacio, et al. Confining Metal-Organic Framework Nanocrystals within Mesoporous Materials: A General Approach via "Solid-State" Synthesis. Chemistry of Materials, vol. 29, No. 22, pp. 9628-9638 (Nov. 28, 2017).

\* cited by examiner

METHOD OF MAKING CONFINED NANOCATALYSTS WITHIN MESOPOROUS MATERIALS AND USES THEREOF

CROSS REFERENCE TO RELATED APPLICATIONS

This is a 371 national stage patent application, which claims priority to PCT International Patent Application No. PCT/US2019/23989, filed 26 Mar. 2019, and titled METHOD OF MAKING CONFINED NANOCATALYSTS WITHIN MESOPOROUS MATERIALS AND USES THEREOF, which is related to and claims priority to U.S. Provisional Patent Application No. 62/647,949, filed on Mar. 26, 2018, entitled "METHOD OF MAKING CONFINED NANOCATALYSTS WITHIN MESOPOROUS MATERIALS AND USES THEREOF," the entire contents of which are incorporated herein by reference.

STATEMENT REGARDING FEDERALLY SPONSORED RESEARCH OR DEVELOPMENT

This invention was made with government support under DE-AR0000811 awarded by the Department of Energy and DE-FE0026432 awarded by the Department of Energy. The government has certain rights in the invention.

1. FIELD

The present disclosure provides methods of making confined nanocatalysts within mesoporous materials (MPMs). The methods utilize solid state growth of nanocrystalline metal organic frameworks (MOFs) followed by controlled transformation to generate nanocatalysts in situ within the mesoporous material. The disclosure also provides applications of the nanocatalysts to a wide variety of fields including, but not limited to, liquid organic hydrogen carriers, synthetic liquid fuel preparation, and nitrogen fixation.

2. BACKGROUND

2.1. Introduction

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Metal organic frameworks (MOFs) have been widely used as versatile precursors for the preparation of catalytically active materials upon applying certain conditions, such as controlled pyrolysis under nitrogen, calcination under oxygen or reduction under hydrogen[1]. Lee, K. J.; Lee, J. H.; Jeoung, S.; Moon, H. R.: Transformation of Metal-Organic Frameworks/Coordination Polymers into Functional Nanostructured Materials: Experimental Approaches Based on Mechanistic Insights, *Accounts of Chemical Research* 2017, 50, 2684-2692. The versatility of MOFs as precursors is mainly due to their unique and highly tunable features, such as well-defined metal sites spaced by organic struts displayed along a crystalline structure with permanent porosity, which can play two simultaneous roles acting as template and precursor. Upon transformation, MOFs can lead to well defined nanostructured catalytically active species, which are monodispersed within hierarchical scaffolds, depending on the conversion conditions, i.e., microporous metal oxide under oxidant conditions or microporous carbonaceous matrix under inert conditions. The resulting nanostructured catalysts can be composed by metals, metal oxides, heteroatom-doped carbon and combinations thereof (Wei, J.; Ge, Q.; Yao, R.; Wen, Z.; Fang, C.; Guo, L.; Xu, H.; Sun, J.: Directly converting $CO_2$ into a gasoline fuel *Nat. Commun* 2017, 8, 15174 doi: 10.1038/ncomms15174).

The use of nano-sized MOF domains (5-50 nm) as precursor instead of bulkier particles can offer some advantages from the catalytic point of view after transformation, as they can lead to the isolation of a reduced number of metallic or metal oxide atoms, and even forming sub-nanometric crystalline domains or denominated clusters (Liu, L. C.; Diaz, U.; Arenal, R.; Agostini, G.; Concepcion, P.; Corma, A.: Generation of subnanometric platinum with high stability during transformation of a 2D zeolite into 3D. *Nature Materials* 2017, 16, 132-138). However, the use of free-standing MOF nanocrystals as precursors is problematic due to their poor stability under high temperatures that may promote their fusion into larger aggregates under the required transformation conditions, thereby leading to the same scenario than starting from bulkier MOF precursors. Therefore, novel synthetic routes are highly demanded to avoid MOF nanocrystalline precursors from sintering during high temperature treatments, thus paving the way to the development of new generation of MOF-derived nanocatalysts.

A general method for selective confinement of MOF nanocrystals within mesoporous materials (MPMs) via 'solid-state' synthesis was recently reported. This versatile approach provides high level of design over the resulting hybrid material formulation and nanoarchitecture, such as composition, loading and dispersion of the MOF guest as well as composition, pore size distribution and particle size of the mesoporous material host. MOF crystalline domains are always restricted to the dimensions delimited by the hosting cavity of the mesoporous material. In the same way, their superior performance as heterogeneous catalysts for synthesis of testosterone derivatives was recently demonstrated (Cirujano, F. G.; Luz, I.; Soukri, M.; Van Goethem, C.; Vankelecom, I. F. J.; Lail, M.; De Vos, D. E.: Boosting the Catalytic Performance of Metal-Organic Frameworks for Steroid Transformations by Confinement within a Mesoporous Scaffold. *Angewandte Chemie International Edition*, 2017, 56, 13302-13306). In addition, $CO_2$ capture capacity as fluidized hybrid sorbents for post-combustion flue gas of these hybrid MOF/MPM materials compared to the 'state-of-the-art', as well as other applications. See PCT Patent Appn. PCT/US2017/046231, Research Triangle Institute.

Recently, Li et al. disclosed the direct conversion of single MOF nanocrystals supported on the external surface of a layered double hydroxide (LDH) into single metal or metal oxide nanocrystals by heating in air or heating under a reductive atmosphere, respectively (Li, P.; Zeng, H. C.: Immobilization of Metal-Organic Framework Nanocrystals for Advanced Design of Supported Nanocatalysts. *ACS Applied Materials & Interfaces* 2016, 8, 29551-29564). The authors note the benefits dispersing and stabilizing effects of the LDH support for obtaining well-dispersed single metal or metal oxide nanocrystals. Li et al. approach does not show nanocatalysts, mesoporous materials as supports or bimetallic MOFs. On page 29552, Li et al. acknowledge that "nanoscale MOFs are unstable and prone to agglomeration and/or deterioration." In addition, the resulting metal and metal oxide nanocrystals supported on this non-porous materials tend to suffer from sintering or fusion into a bulk phase.

3. SUMMARY OF THE DISCLOSURE

The present disclosure provides a method of preparing a confined metallic nanocatalyst within a mesoporous material (MPM) which comprises: (a) impregnating at least one or more organic compound, comprising one or more multidentate ligand(s) $[A_x(L^{-x})]$ capable of forming coordination bonds with at least one metal ion, on the mesoporous material to form a first intermediate $[(A_x(L^{-x})/MPM)]$; (b) exposing the first intermediate $[(A_x(L^{-x})/MPM)]$ to an acid in gas phase to form a second intermediate $[(H_x(L^{-x})/MPM)]$; (c) adding to the second intermediate $[(H_x(L^{-x})/MPM)]$ a solvent solution of one or more metal ions ($M_1^{+y}$, $M_2^{+y}$, $M_3^{+y}$) so as to form coordination bonds with the one or more multidentate ligand(s) forming a metal organic framework (MOF) precursor confined within a mesoporous material [MOF/MPM], and (d) treating the precursor of step (c) [MOF/MPM] under controlled transformation conditions so as to form the metallic nanocatalyst confined within the mesoporous material.

In the method above, step (d) further may comprise step (d)(1) comprising contacting the precursor of step (c) [MOF/MPM] with one or more organic compounds (Z) to make a second multidentate ligand capable of forming coordination bonds [Z/MOF/MPM]; and step (d)(2) adding a solvent solution of one or more additional metal ion to form a modified MOF precursor with additional metals confined within the mesoporous material [MOF/MPM].

In the method above, the chelating ligand (Z) in step (d)(1) comprises a metal binding site for complexing a second metal ion.

In some embodiments, the controlled transformation conditions cause greater than 90% of the carbon in the MOF to be released from the MOF/MPM. In some cases, nearly 100% of the carbon may be released, e.g., greater than 95%, greater than 97%, greater than 99%.

In other embodiments, the controlled transformation conditions lead to 50%±10% of the carbon in the MOF to be released from the MOF/MPM. Alternatively, 30%±10%, 40%±10%, 60%±10% or 70%±10% may be released.

In some embodiments, the treating under controlled transformation conditions is pyrolysis at a temperature of about 300° C. to about 1000° C. in an inert gas atmosphere. More specifically, the inert atmosphere pyrolysis may be at 350° C.±50° C., 400° C.±50° C., 450° C.±50° C., 500° C.±50° C., 550° C.±50° C., 600° C.±50° C., 650° C.±50° C., 700° C.±50° C., 750° C.±50° C., 800° C.±50° C., 850° C.±50° C., 900° C.±50° C., or 950° C.±50° C.

In other embodiments, the treating under controlled transformation conditions is calcination at a temperature of about 300° C. to about 600° C. in an atmosphere containing oxygen gas. More specifically, the calcination may be at 350° C.±50° C., 400° C.±50° C., 450° C.±50° C., 500° C.±50° C., or 550° C.±50° C. The calcination atmosphere may be air. Alternatively, the calcination atmosphere may be enriched with oxygen or air depleted in oxygen but still containing a sufficient concentration of oxygen to react with the carbon in the MOF/MPM.

In still other embodiments, the treating under controlled transformation conditions is treatment in a reductive atmosphere, such as reduction with hydrogen at a temperature of about 25° C. to about 300° C. More specifically, the calcination may be at 50° C.±25° C., 75° C.±25° C., 100° C.±25° C., 125° C.±25° C., 150° C.±25° C., 175° C.±25° C., 200° C.±25° C., 225° C.±25° C. 250° C.±50° C., or 275° C.±25° C. The reductive atmosphere may be 100% hydrogen, 90±5% hydrogen, 80±5% hydrogen, 70±5% hydrogen, 60±5% hydrogen, 50±5% hydrogen, 40±5% hydrogen, 30±5% hydrogen, 20±5% hydrogen, or 10±5% hydrogen.

In some embodiments, the confined nanocatalyst is monometallic ($M_1$).

In other embodiments, the confined nanocatalyst is bimetallic ($M_1+M_2$).

In still other embodiments, the confined nanocatalyst has 3 or more metals.

In one embodiment, the confined nanocatalyst within the mesoporous material has a diameter of less than 10 nm. In other embodiments, the nanocatalyst has a diameter of about 2 to about 4 nm, about 3 to about 5 nm, about 4 to about 6 nm, about 5 to about 7 nm, about 6 to about 8 nm, about 7 to about 9 nm, or about 8 to about 10 nm.

In one embodiment, the mesoporous material is a mesoporous metal oxide, a mesoporous silica, a mesoporous carbon, a mesoporous polymer, a mesoporous silicoalumina (zeolite), a mesoporous organosilica, or a mesoporous aluminophosphate. The mesoporous metal oxide may be aluminum oxide, cerium oxide, titanium oxide, zirconium oxide, or magnesium oxide.

In one embodiment, the mesoporous material has a surface area of about 100 m$^2$/g to about 1000 m$^2$/g.

In one embodiment, the metal ions ($M_1^{+y}$, $M_2^{+y}$, $M_3^{+y}$) are selected from the group consisting of Al, Au, Ce, Co, Fe, Jr, Mo, Ni, Pd, Rh, Ru, Ti, V and Zr or combinations thereof. Specific reactions and metal catalyst combinations are as follows:

Alkene ammoxidation reactions (Bi—Mo, V—Mo, V—Sb, Fe—Sb, Cr—Sb, Cr—Nb, Fe—Nb), James F. Brazdil *Catalysts* 2018, 8(3), 103; doi:10.3390/catal8030103.

Alkene epoxidation (Mn—Fe), Vincent Escande, Eddy Petit, Laetitia Garoux, Clotilde Boulanger, and Claude Grison *ACS Sustainable Chem. Eng.,* 2015, 3 (11), pp 2704-2715.

Ammonia synthesis (Co—Mo, Fe—Mo), Yuki Tsuji, Masaaki Kitano, Kazuhisa Kishida, Masato Sasase, Toshiharu Yokoyama, Michikazu Hara and Hideo Hosono *Chem. Commun.,* 2016, 52, 14369-14372.

Carboxylation reactions (Ni—Zn), Qiang Liu, Lipeng Wu, Ralf Jackstell & Matthias Beller *Nature Communications,* 2015, 6, 5933.

$CO_2$ methanation reactions (Zr—Ce, Ni—Ce, N—Ti), F Ocampo F, B Louis, A Kiennemann, A C Roger IOP Conf. Series: Materials Science and Engineering 19 (2011) 012007.

Direct methanol synthesis from methane (Fe—Mo, Ni—Mg, Co—Mo), Manoj Ravi, Marco Ranocchiari and Jeroen A. van Bokhoven *Angew. Chem. Int. Ed.* 2017, 56, 16464.

Dry-methane reforming (Ni—Mg, Ni—Al), Radosław Dębek, Maria Elena Galvez, Franck Launay, Monika Motak, Teresa Grzybek & Patrick Da Costa *International Journal of Hydrogen Energy,* 2016, 41, 11616-11623.

Electrocatalytic ammonia oxidation (Ru—Zr, Pt—Ir, Pt—Pd) Denver Cheddie "Ammonia as a Hydrogen Source for Fuel Cells: A Review" Chapter 13 from a book edited by Dragica Minic called "Hydrogen Energy—Challenges and Perspectives".

Catalytic converters for internal combustion engines, (Pt—Rh, Ce—Pt—Rh) Farrauto and Heck, Catalytic converters: state of the art and perspectives, *Catalysis Today,* 1999, 51(3-4), 351-360.

In one embodiment, the multidentate ligand for the MOF is selected from the group consisting of, terephthalate, benzene-1,3,5-tricarboxylate, 2,5-dioxibenzene dicarboxylate, biphenyl-4,4'-dicarboxylate, imidazolate, pyrimidineazolate, triazolate, tetrazolate, derivatives or combinations thereof.

In some embodiments, the MOF may be HKUST-1, $M_2$(dobpdc), MIL-100, MIL-101, MIL-53, MOF-74, NU-1000, PCN-222, PCN-224, UiO-66, UiO-67, ZIF-8, ZIFs, or derivatives thereof.

In one embodiment, wherein the mesoporous material is selected from the group consisting of, MCM-41, SBA-15, or commercially available silica.

In one embodiment, wherein the free functional groups at the organic ligand of the MOF are selected from amino, bipyridine, chloride, hydroxyl, porphyrin, ester, amide, ketone, acid, hydrazine, or oxime.

In one embodiment, wherein the chelating ligand (Z) is selected from salicyl aldehyde, ethyl chloro-oxoacetate, pyridine aldehyde, hydroxymethylphosphine, pyrrole aldehyde, ethylenediamine, picolinate, dimethylglyoximate, 2,2',2''-terpyridine, 1,4,7,10-triethylenetetramine, 1,4,8,11-triethylenetetramine, phenanthroline and bisdiphenylphospinoethane or phosphine aldehyde.

In some embodiments, the nanocatalyst confined within mesoporous material is further reacted with additional organometallic metal complexes or metal salts with polymers, organometallic ligand precursors, nitrogen-containing organic compounds, phosphorous-containing organic compounds, sulfur-containing organic compounds, boron-containing organic compounds, halide salts, organic halides, or metal atoms added via atomic layer deposition or chemical vapor deposition.

The disclosure also provides a catalyst made by the methods described above.

The catalyst may further comprise an added metal promotor.

The disclosure also provides uses. The catalysts described above may be used to catalyze alkene ammoxidation reactions, alkene epoxidation, ammonia synthesis, carboxylation reactions, $CO_2$ methanation reactions, conversion of $CO_2$ to fuel, direct methanol synthesis from methane, dry-methane reforming, electrocatalytic ammonia oxidation, electrocatalytic oxygen reduction reactions, Fischer-Tropsch synthesis, hydro-/dehydrogenation of liquid organic hydrogen carriers, hydrotreating and hydroprocessing esterification reactions, methanol synthesis from syngas, reverse water-gas shift reactions, or water-gas shift reactions.

4. BRIEF DESCRIPTION OF THE FIGURES

FIG. 1. Scheme describing a general approach of single-nanocrystal-to-single-nanocatalyst conversion of MOF nanocrystals into bimetallic oxide nanocatalysts. TEM images (a) SBA-15 and (b) (Zr)UiO-66($NH_2$)/SBA-15. STEM images for (c) PdCl—SI—(Zr)UiO-66($NH_2$)/SBA-15 and (d) $Pd_{NC}$/SI—(Zr)UiO-66($NH_2$)/SBA-15.

Figure 2:
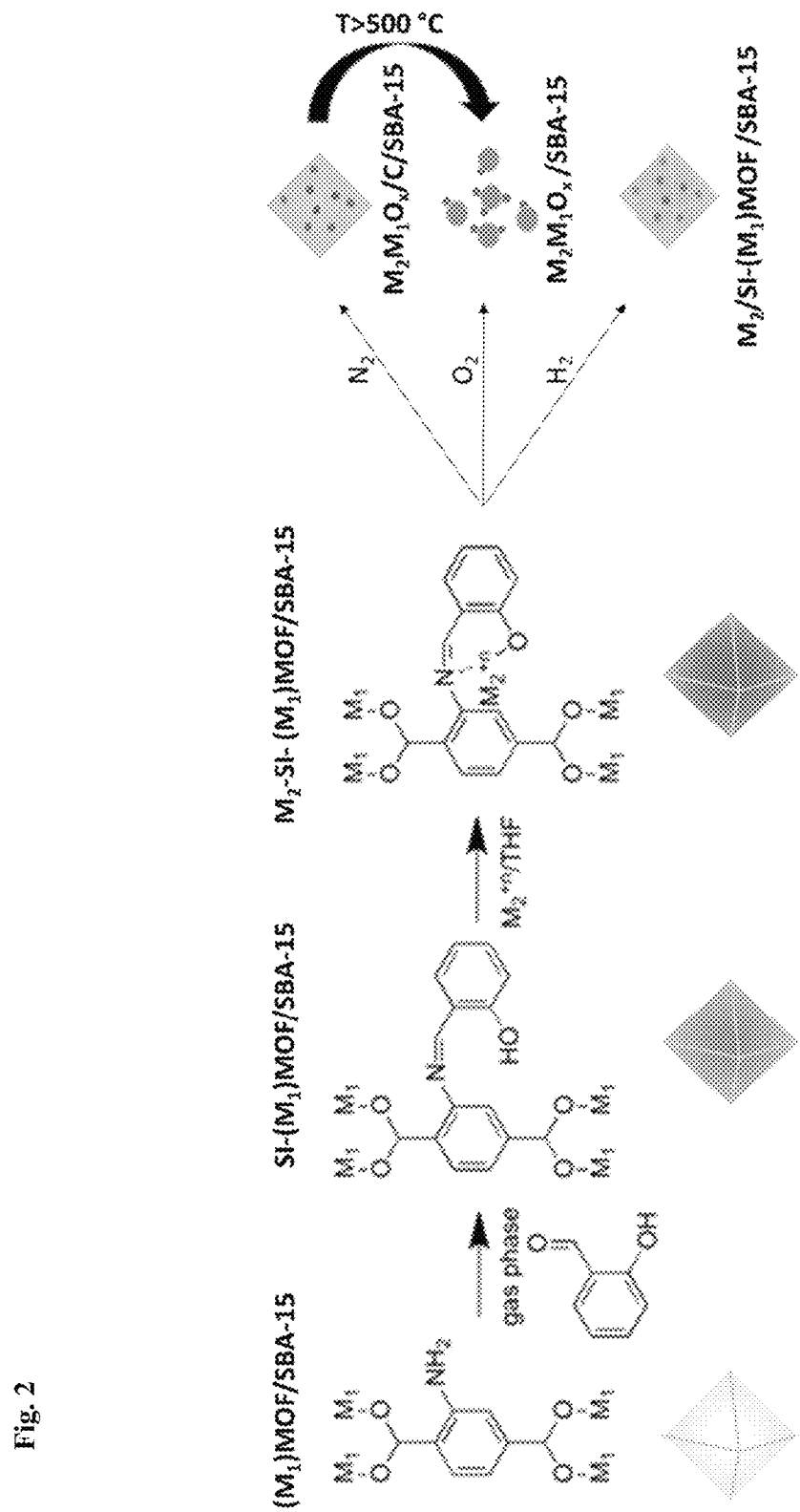

FIG. 2. A scheme showing a two-step post-synthesis modification (PSM) for transition metal complex incorporation on MOF nanocrystals and subsequently controlled transformation treatment for preparing bimetallic nanocatalysts. This controlled transformation treatment scheme is valid for monometallic MOF nanocrystals containing only one metal oxide at the SBU. Low MOF loading (below 15 wt %) has been found to be a determinant for obtaining sufficient initial spacing between MOF nanocrystals. Higher MOF loadings (20-40 wt. %) lead to shorter distances between crystallites, and thereby, higher tendency to form aggregates during the transformation treatment.

Figure 3:
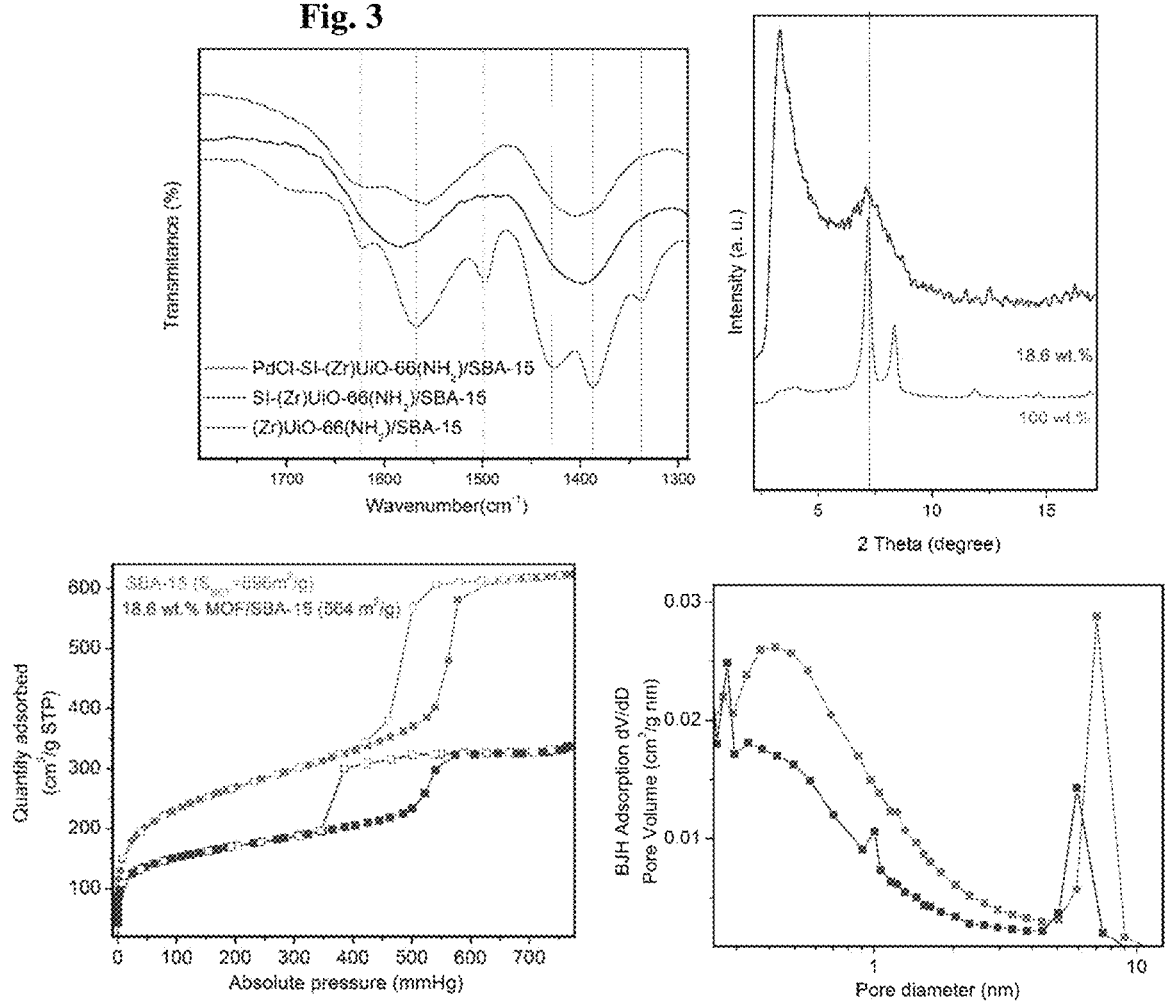

FIG. 3. Typical characterization routine for bimetallic [$M_2$-Z-($M_1$)MOF/MPM] precursor materials: FTIR, XRD, surface area and pore distribution.

Figure 4A:
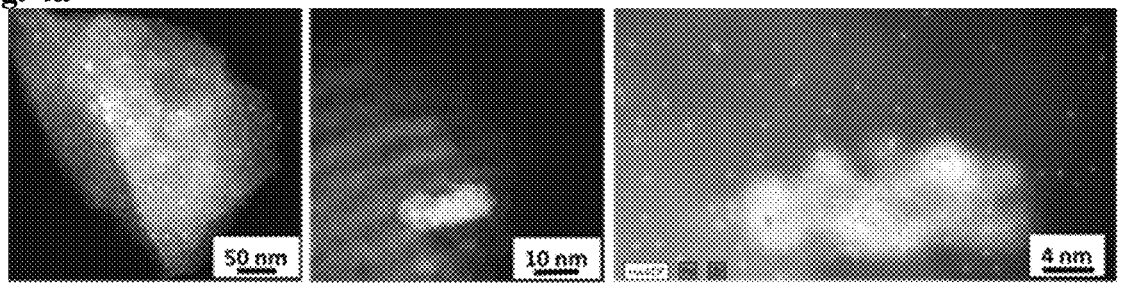

FIG. 4a. STEM images and EDS for carbon-free $PdZrO_2$ nanocatalysts confined within SBA-15 prepared from Pd—SI—(Zr)UiO-66($NH_2$)/SBA-15 treated via pyrolysis under nitrogen at 650° C.

Figure 4B:
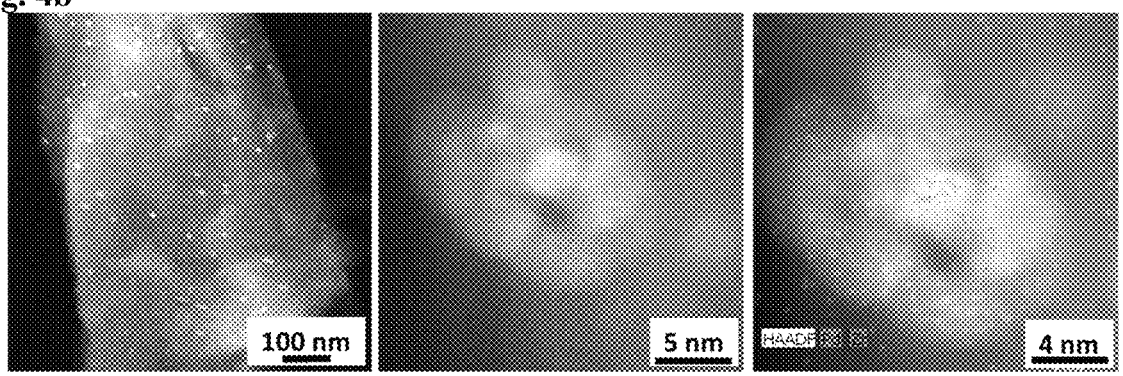

FIG. 4b. STEM images and EDS for $PdZrO_2$ nanocatalysts confined within SBA-15 prepared from Pd—SI—(Zr)UiO-66($NH_2$)/SBA-15 treated via calcination under oxygen at 500° C.

Figure 4C:
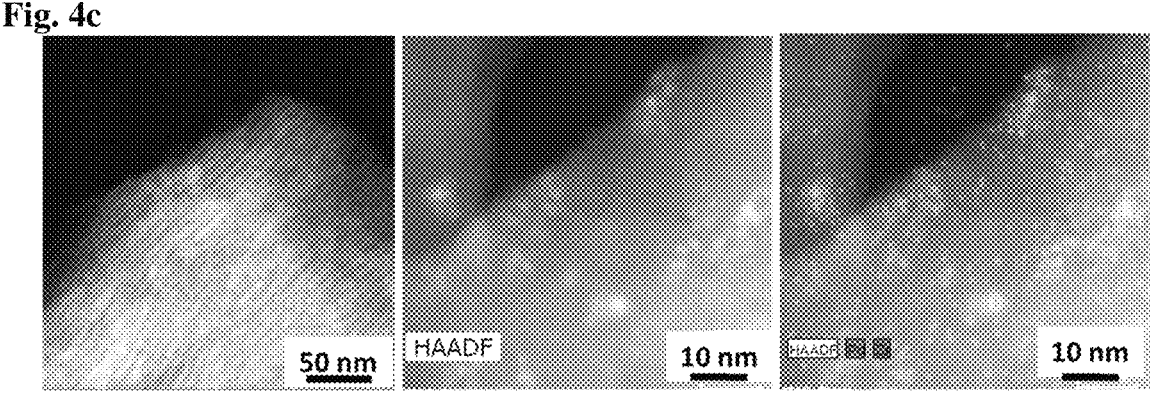

FIG. 4c. STEM images and EDS for PdNc/(Zr)UiO-66($NH_2$) nanocatalysts confined within SBA-15 prepared from Pd—SI—(Zr)UiO-66($NH_2$)/SBA-15 treated via reduction under hydrogen at 200° C.

Figure 5:
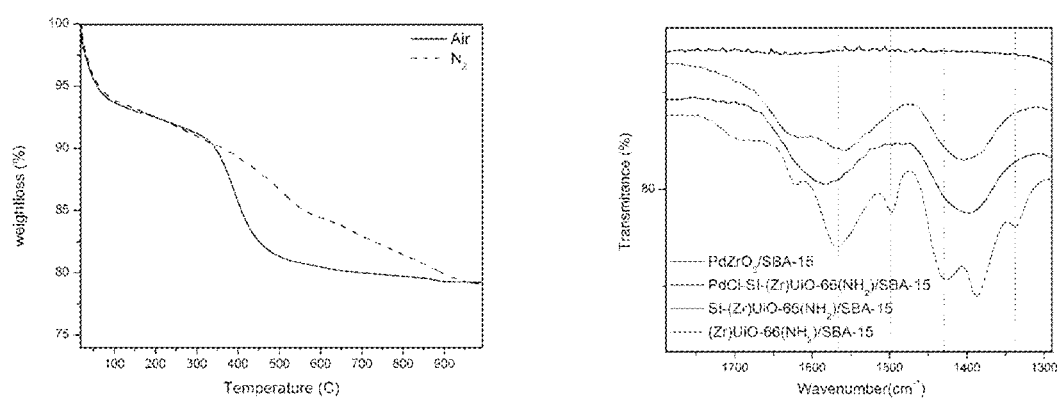

FIG. 5. (left) TGA profiles for sample PdCl—SI—(Zr)UiO-66($NH_2$)/SBA-15 under nitrogen and air. (right) FTIR spectra of consecutive steps for the preparation of $PdZrO_2$/SBA-15 sample via pyrolysis under nitrogen at 900 C, as shown in FIG. 1.

Figure 6:
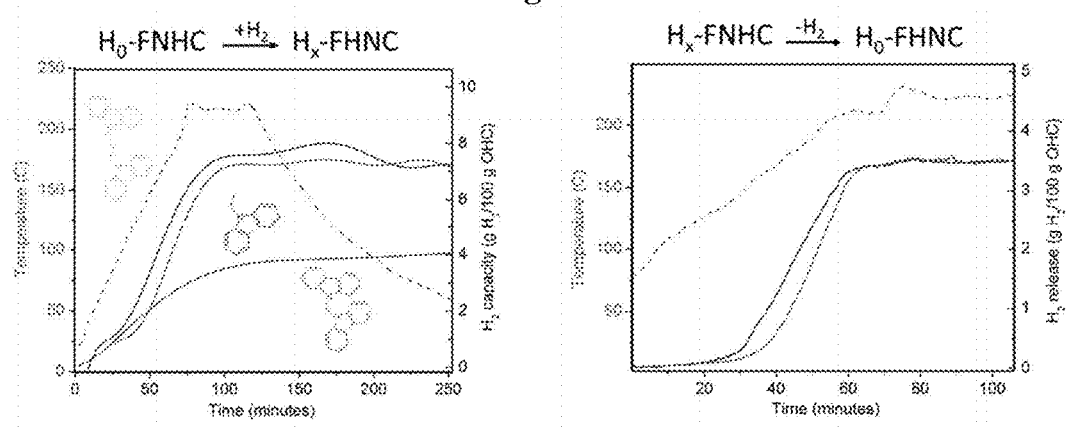

FIG. 6. Application example, results for hydro-/dehydrogenation of liquid organic hydrogen carriers in solid state.

Figure 7:
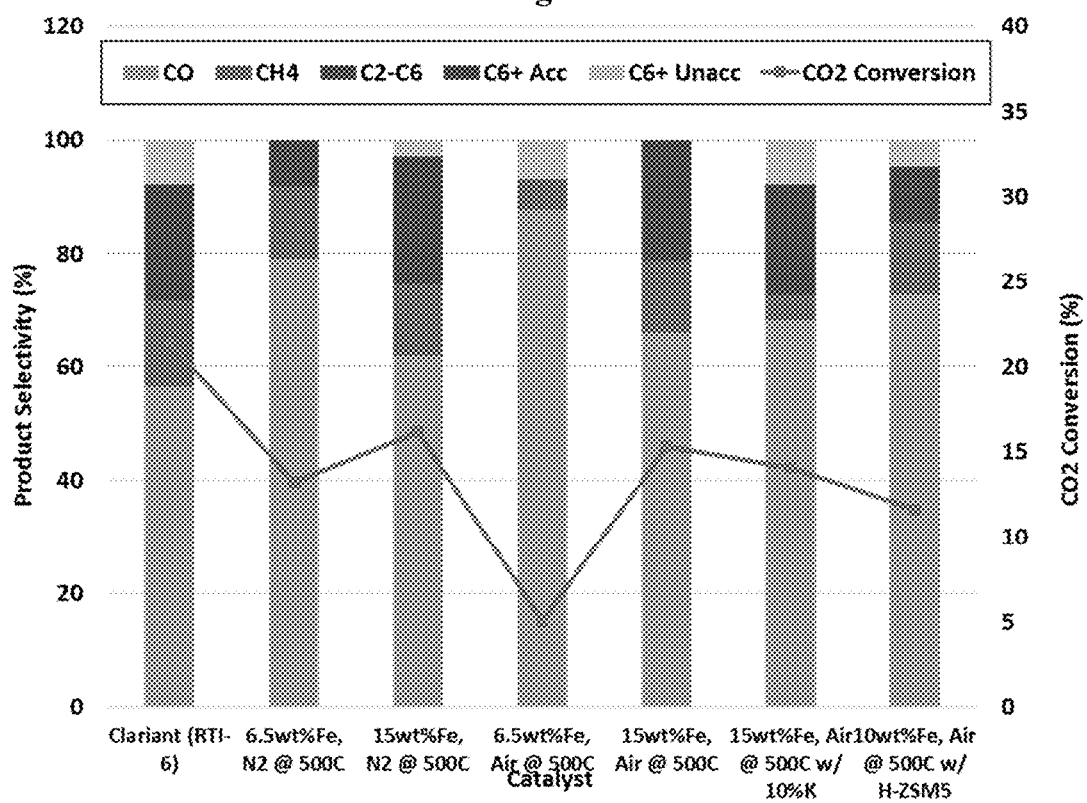

FIG. 7. Application example of some results for $CO_2$ to fuels reaction catalyzed by $Fe_3O_4$/$SiO_2$ and $FeC/SiO_2$ catalysts at varying loadings prepared from (Fe)MIL-100/$SiO_2$ compared to Clariant commercial catalysts.

Figure 8:
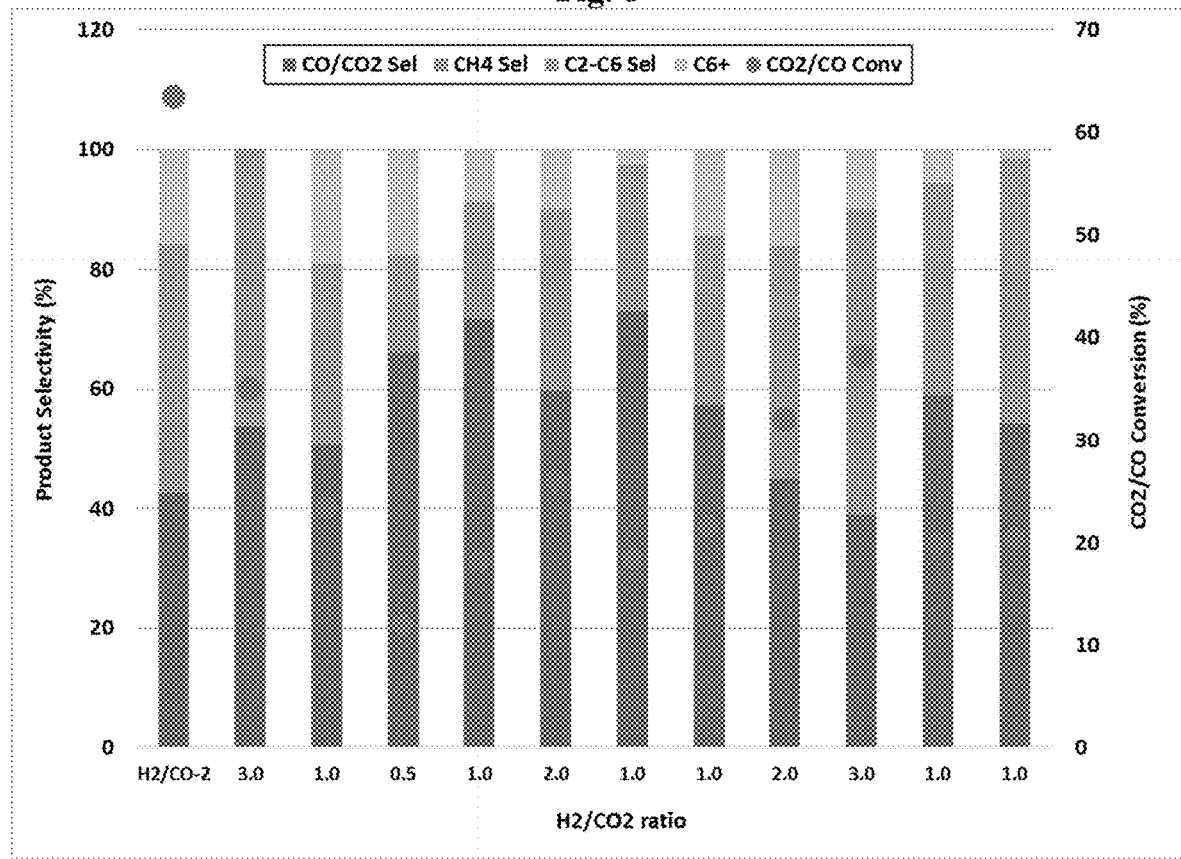

FIG. 8. Application example of different $CO_2$ to fuels reaction catalyzed by $FeC/SiO_2$ at various ratio of $H_2/CO_2$.

5. DETAILED DESCRIPTION OF THE DISCLOSURE

This disclosure provides a novel strategy to prepare nano-sized catalyst via controlled transformation of MOF nanocrystals. These catalysts may be optionally decorated with additional organometallic metal complexes or metal salts previously or afterwards confined within mesoporous materials and or optionally decorated with polymers, organometallic ligand precursors, nitrogen-containing organic compounds, phosphorous-containing organic compounds, sulfur-containing organic compounds, boron-containing organic compounds, halide salts, organic halides, metal atoms added via atomic layer deposition or chemical vapor deposition or other compounds previously or afterwards confined within mesoporous materials. This general method preserves the dispersion, nano-sized dimension, and 3-D distribution along the mesoporous matrix of the pristine support precursor into the resulting catalysts, thus favoring the formation of nanometric and subnanometric active species (such as metals, metal oxides, N-doped carbons, P-doped carbons, S-doped carbons, B-doped carbons, halide-doped carbons, and combinations thereof) with high precision by using proper selection of the hybrid precursors, (i. e., organometallic metal complex, metal salt, polymer, organometallic ligand precursor, nitrogen-containing organic, phosphorous-containing organic, sulfur-containing organic, boron-containing organic, halide salts, organic halides, MOF and mesoporous scaffold).

In preferred embodiments, the transformation treatment can be done at three different conditions: pyrolysis, calcination or reduction. Additional properties are conferred by confining the resulting supported nanocatalysts in the mesoporous scaffold, such as enhanced diffusion, improved chemical stability, excellent attrition resistance as well as feasible handling, as recently reported for the hybrid MOF/

MPMs materials (Luz, I.; Soukri, M.; Lail, M.: Confining Metal-Organic Framework Nanocrystals within Mesoporous Materials: A General Approach via "Solid-State" Synthesis. *Chemistry of Materials* 2017 29 9628-9638).

MOFs have been widely used as versatile precursors for preparation of catalytically active materials upon applying certain conditions, such as controlled pyrolysis under nitrogen or other inert gas, calcination under oxygen or reduction under hydrogen or other reducing gas. The resulting solid catalysts can be composed of metals, metal oxides, nitrogen-doped carbon, phosphorous-doped carbon, sulfur-doped carbon, boron-doped carbon, halide-doped carbon, and combinations thereof (Wei et al. 2017). The use of nano-sized MOF domains (5-50 nm diameter) as precursor instead of bulkier particles can offer some advantages from the catalytic point of view, as they can lead to the isolation of a reduced number of metallic atoms in a single crystal, or cluster (Liu, L. C.; Diaz, U.; Arenal, R.; Agostini, G.; Concepcion, P.; Corma, A.: Generation of subnanometric platinum with high stability during transformation of a 2D zeolite into 3D. *Nature Materials* 2017, 16, 132-138), upon one of the treatments mentioned above. However, the use of free-standing bulk MOF nanocrystals as precursors is problematic due to the large amount of inaccessible metal sites concentrated deep in sub-surface regions of the resulting material and their poor stability under high temperatures that gives rise their fusion into larger aggregates upon applying those required transformation treatments. Therefore, novel synthetic routes are highly demanded to confine the concentration of nanocatalysts derived from MOF to the catalyst surface and to avoid MOF nanocrystals from sintering during high temperature treatments, thus paving the way to the development of new generation of MOF-derived nanocatalysts.

Our group recently reported a novel method for selectively supporting MOF nanocrystals within mesoporous materials via 'solid-state' crystallization. This versatile approach provides a high level of design over the resulting hybrid material formulation and nanoarchitecture, such as composition, loading and dispersion of the MOF guest as well as composition, pore size distribution and particle size of the mesoporous material host. MOF nanocrystal size is always restricted to the dimensions delimited by the hosting cavity of the mesoporous material. In the same way, we have recently demonstrated the superior catalytic activity as heterogeneous catalysts for synthesis of testosterone derivatives (Cirujano et al. 2017) In addition, these materials have $CO_2$ capture capacity as fluidized hybrid sorbents for post-combustion flue gas of hybrid MOF/MPM materials compared to the 'state-of-the-art', as well as other applications, such as chromatography. See PCT Patent Appn. PCT/US2017/046231, Research Triangle Institute.

Herein, we demonstrate that those supported and well-dispersed MOF nanocrystals can be used as optimal precursor for preparing either nanosized mono-, bi-, or multimetallic metal oxides through a single-nanocrystal-to-single-nanocatalyst transformation, which can be done upon 1) pyrolysis under nitrogen or other inert gas (from 500 to 1000° C.), 2) calcination in the presence of oxygen (400-800° C.) or 3) chemical reduction under hydrogen or other suitable reducing gas (from room temperature to 300° C.). This approach preserves the initial 3D distribution of the MOF precursors on the resulting nanocatalysts along the surface area of the mesoporous material, thus avoiding the tendency of nanocrystals to fuse into larger crystallites (Prieto, G.; Zecevic, J.; Friedrich, H.; de Jong, K. P.; de Jongh, P. E.: Towards stable catalysts by controlling collective properties of supported metal nanoparticles. *Nature Materials* 2013, 12, 34-39), which is one of the major causes of deactivation for supported catalysts. Therefore, more stable and highly active subnanometric catalysts (<1 nm) have been prepared by our general strategy and tested for some catalytic reactions of highly industrial interest, such as hydro-/dehydrogenation of liquid organic hydrogen carriers, direct methanol synthesis from methane, methanol synthesis from syngas, $CO_2$ methanation, ammonia synthesis, Fischer-Tropsch synthesis, dry-methane reforming, alkene epoxidation, water-gas shift, reverse water-gas shift, hydrotreating and hydroprocessing esterification, carboxylation, electrocatalytic oxygen reduction reaction, electrocatalytic ammonia oxidation, alkene ammoxidation, catalytic combustion, and $CO_2$ to fuels, among others.

In a first step, an aqueous solution of an organic ligand salt of the formula $A_x(L^{-x})$ is contacted with a mesoporous material (MPM) present at a concentration in the range of 10-300 mg/mL, preferably 25-275 mg/mL, preferably 50-250 mg/mL to form an impregnated mesoporous salt material of the formula $A_x(L^{-x})$/MPM. Exemplary salts include, but are not limited to, mineral or organic acid salts of basic groups such as amines, and alkali or organic salts of acidic groups such as carboxylic acids. The salts include, but are not limited to, the conventional non-toxic salts or the quaternary ammonium salts of the parent compound formed, for example, from non-toxic inorganic or organic acids. Salts of carboxylic acid containing ligands may include cations such as lithium, sodium, potassium, magnesium, additional alkali metals, and the like. The salts include, but are not limited to, the conventional non-toxic salts or the quaternary ammonium salts of the parent compound formed, for example, from non-toxic inorganic or organic acids. In a preferred embodiment, the salts are alkali metal salts, most preferably sodium salts. In a preferred embodiment, the contacting is performed at a temperature of up to 80° C., preferably 10-80° C., preferably 15-60° C., preferably 20-40° C., preferably 22-30° C., or about room temperature and has a contacting time of up to 48 hours, preferably 0.5-36 hours, preferably 1-24 hours, preferably 2-12 hours, preferably 2.5-8 hours, preferably 3-6 hours. In some embodiments, the ligand (i.e. acid form; 2,6-dihydoxyterephthalic acid) may be dissolved and impregnated in water or organic solvents. Exemplary organic solvents include, but are not limited to, methanol, ethanol, tetrahydrofuran, N,N-dimethylformamide, acetonitrile, acetone, and the like.

In a second step, the impregnated mesoporous salt material present at a concentration in the range of 10-300 mg/mL, preferably 25-275 mg/mL, preferably 50-250 mg/mL is treated with a gas phase acid to form an impregnated mesoporous acid material of the formula $H_x(L^{-x})$/MPM. The gas phase acid may be an inorganic acid such as HCl. In a preferred embodiment, the gas treatment is performed at a temperature of up to 150° C., preferably 10-120° C., preferably 15-110° C., preferably 20-40° C., preferably 22-30° C., or about room temperature and has a treating time of up to 48 hours, preferably 0.5-36 hours, preferably 1-24 hours, preferably 2-12 hours, preferably 2.5-8 hours, preferably 3-6 hours. The temperature will depend on the choice of the acid. An organic acid may be at a temperature of 100° C.±50° C., preferably 100° C.±20° C., preferably 100° C.±10° C., preferably 100° C.±5° C. Whereas treatment with nitrogen saturated with HCl might be a 30° C.±20° C., preferably 30° C.±10° C., preferably 30° C.±5° C.

Alternatively, the bound ligand may be treated with an aqueous acidic solution of 0.05-10.0 M in concentration, preferably 0.1-9.0 M, preferably 1.0-8.0M, preferably 2.0-

6.0 M, or about 4.0 M to form an impregnated mesoporous acid material of the formula $H_x(L^{-x})$/MPM. Strong acids including, but not limited to, HCl, $H_2SO_4$, and $HNO_3$ are preferred, but organic acids and weak acids (i.e. acetic acid) may also be used in the treating, most preferably HCl. In a preferred embodiment, the solution treatment is performed at a temperature of up to 80° C., preferably 10-80° C., preferably 15-60° C., preferably 20-40° C., preferably 22-30° C., or about room temperature and has a treating time of up to 48 hours, preferably 0.5-36 hours, preferably 1-24 hours, preferably 2-12 hours, preferably 2.5-8 hours, preferably 3-6 hours.

In a third step, the impregnated mesoporous acid material, present at a concentration in the range of 10-300 mg/mL, preferably 25-275 mg/mL, preferably 50-250 mg/mL, is contacted with an aqueous solution of a metal precursor of the formula $M^{+y}$ to form an impregnated mesoporous metal organic framework precursor. In a preferred embodiment, the contacting is performed at a temperature of up to 80° C., preferably 10-80° C., preferably 15-60° C., preferably 20-40° C., preferably 22-30° C., or about room temperature and has a contacting time of up to 48 hours, preferably 0.5-36 hours, preferably 1-24 hours, preferably 2-12 hours, preferably 2.5-8 hours, preferably 3-6 hours.

In a next step the impregnated mesoporous metal organic framework precursor is heated in the absence of a solvent or exposed to a volatile vapor (i.e. and amine such as methylamine or controlled moisture such as steam) in the absence of a solvent to form a hybrid material of the formula $(M^{+y}L^{-x})$/MPM, or hereafter called MOF/MPM. In this step, the metal ions form coordinate bonds with the one or more organic ligands, preferably multidentate organic ligands to form a nano-crystalline metal organic framework in the pore spaces of the mesoporous material. In a preferred embodiment, the heating is performed at a temperature of up to 300° C., preferably 40-250° C., preferably 60-220° C., preferably 100-200° C., preferably 120-190° C., and has a heating time of up to 60 hours, preferably 12-48 hours, preferably 24-36 hours. In a preferred embodiment, the exposing to a vapor is performed at a temperature of up to 80° C., preferably 10-80° C., preferably 15-60° C., preferably 20-40° C., preferably 22-30° C., or about room temperature and has a heating time of up to 48 hours, preferably 6-36 hours, preferably 12-24 hours. In certain embodiments, a catalytic amount of a specific additive including (preferably 15%), but not limited to, methanol, ethanol, tetrahydrofuran, N,N-dimethylformamide, and the like may be employed to assist the crystal formation within the hybrid material.

In some embodiments, the MOF/MPM is treated with an organic compound to form another ligand and then treated with at least one or multiple additional metal to create a bound with the MOF. Collectively, whether mono-metallic, bimetallic, trimetallic or multimetallic, those metals will become part of the MOF confined with the MPM for the next step. In other embodiments, the MOF/MPM (mono-, bi-, tri-, polymetallic) is contacted with a solution containing salts of additional metal catalysts or promoters. The modified MOF/MPM is then dried and treated with the controlled transformation conditions described below.

In a final step, the embedded MOF or MOF/MPM is subjected to controlled transformation conditions to generate the confined nanocatalyst. The controlled transformation may be (1) pyrolysis under nitrogen or other inert gas: where nanocrystals are obtained when the transformation is carried out under nitrogen (or other inert gas such as Ar or a reactive gas such as acetylene) for temperatures ranging from 300° C. to 1000° C. In some embodiments, the temperatures ranging from 300° C. to 500° C., preferably 400-600° C., preferably 500-700° C., preferably 600-800° C., preferably 700-900° C., preferably 800-1000° C.

Alternatively, the controlled transformation may be (2) calcination in an oxygen containing atmosphere. All organic materials are released at lower temperatures when an oxygen containing atmosphere is present in the transformation treatment. Carbon-free nanocatalysts are obtained for temperatures of 300-600° C., preferably 300-350° C., preferably 400-450° C., preferably 450-500° C., preferably 500-550° C., preferably 550-600° C.

Alternatively, the controlled transformation may be (3) reduction with an atmosphere containing hydrogen. When hydrogen is present in the atmosphere for transformation the temperatures are still milder (from room temperature to 300° C.). The MOF carbon microstructure is not completely decomposed, although the transition metal cations decorating the MOF nanocrystal are reduced to form a metallic nanocrystal confined within the microporous cavities of the MOF and/or MPM. In some embodiments, the temperature for the reductive transformation is from 25-50° C., preferably 50-75° C., preferably 75-100° C., preferably 100-125° C., preferably 125-150° C., preferably 150-175° C., preferably 175-200° C., preferably 200-225° C., preferably 225-250° C., preferably 250-275° C., preferably 275-300° C.

In certain embodiments, the confined metallic nanocrystal is present only within the mesopores or void spaces of the mesoporous material and homogeneously dispersed within the mesopores or void spaces of the mesoporous material. As used herein, "disposed on", "embedded" or "impregnated" describes being completely or partially filled throughout, saturated, permeated and/or infused. The confined metallic nanocrystal may be affixed substantially within the pore space of the mesoporous material. The confined metallic nanocrystal may be affixed to the mesoporous material in any reasonable manner, such as physisorption or chemisorption and mixtures thereof. In one embodiment, greater than 10% of the pore spaces of the mesoporous material is occupied by the confined metallic nanocrystal, preferably greater than 15%, preferably greater than 20%, preferably greater than 25%, preferably greater than 30%, preferably greater than 35%, preferably greater than 40%, preferably greater than 45%, preferably greater than 50%, preferably greater than 55%, preferably greater than 60%, preferably greater than 65%, preferably greater than 70%, preferably greater than 75%, preferably greater than 80%, preferably greater than 85%, preferably greater than 90%, preferably greater than 95%, preferably greater than 96%, preferably greater than 97%, preferably greater than 98%, preferably greater than 99%. Alternatively, 5-10% of the pore spaces of mesoporous material may be occupied.

In certain embodiments, the confined metallic nanocrystal is substantially present only within the mesopores or void spaces of the mesoporous material and homogeneously dispersed on the external surface of the mesoporous material, preferably greater than 60% of the confined metallic nanocrystal is located in the pore spaces and not at the surface of the mesoporous material, preferably greater than 70%, preferably greater than 75%, preferably greater than 80%, preferably greater than 85%, preferably greater than 90%, preferably greater than 95%, preferably greater than 96%, preferably greater than 97%, preferably greater than 98%, preferably greater than 99%. As used herein, homogeneous dispersion refers to dispersion in a similar or the same manner and may refer to uniform structure and composition. The coefficient of variation of the nanocatalysts are distributed in the MPM is less than 10%, preferably less than 8%, preferably less than 6%, preferably less than 5%, preferably less than 4%, preferably less than 3%, preferably less than 2%. The surface of the MPM is generally substantially free from the nanocatalysts.

In certain embodiments, the method further comprises drying at least one selected from the group consisting of the impregnated mesoporous salt material, the impregnated mesoporous acid material, the impregnated mesoporous metal organic framework precursor, and the hybrid material at a temperature in the range of 25-160° C., preferably 85-150° C., preferably 90-140° C., preferably 100-130° C., or about 120° C. under a vacuum and with a drying time of up to 24 hours, preferably 0.5-18 hours, preferably 1-12 hours, preferably 1.5-6 hours, or about 2 hours.

In certain embodiments, the method further comprises washing the hybrid material with distilled water or other polar protic solvent and extracting water from the hybrid material in a Soxhlet system recycling methanol or other polar protic solvent.

In a preferred embodiment, the mesoporous material is at least one selected from the group consisting of a mesoporous metal oxide (aluminum oxide, cerium oxide, titanium oxide, zirconium oxide, magnesium oxide, etc.), a mesoporous silica, a mesoporous carbon, a mesoporous polymer, a mesoporous silicoalumina (zeolite), a mesoporous organosilica, and a mesoporous aluminophosphate, etc.). As used herein, a mesoporous material may refer to a material containing pores with diameters between 2-50 nm, porous materials are classified into several kinds by their pore size. In a preferred embodiment, the mesoporous material has a percent porosity of greater than 10%, preferably greater than 20%, preferably greater than 25%, preferably greater than 30%, preferably greater than 35%, preferably greater than 40%

In a preferred embodiment, the organic ligand ($L^{-x}$) of the organic ligand salt is at least one selected from the group consisting of polycarboxylate ligands, azaheterocyclic ligands, and derivatives thereof. As used herein, "ligand" refers to a mono-dentate or polydentate compound that bind a transition metal or a plurality of transition metals, respectively. Generally, a linking moiety comprises a substructure covalently linked to an alkyl or cycloalkyl group, comprising 1 to 20 carbon atoms, an aryl group comprising 1 to 5 phenyl rings, or an alkyl or aryl amine comprising alkyl or cycloalkyl groups having from 1 to 20 carbon atoms or aryl groups comprising 1 to 5 phenyl rings, and in which a linking cluster (e.g., a multidentate function groups) are covalently bound to the substructure. A cycloalkyl or aryl substructure may comprise 1 to 5 rings that comprise either of all carbon or a mixture of carbon with nitrogen, oxygen, sulfur, boron, phosphorus, silicon and/or aluminum atoms making up the ring. Typically, the linking moiety will comprise a substructure having one or more carboxylic acid linking clusters covalently attached.

In a preferred embodiment, the organic ligand ($L^{-x}$) of the organic ligand salt is at least one selected from the group consisting of, terephthalate, benzene-1,3,5-tricarboxylate, 2,5-dioxibenzene dicarboxylate, biphenyl-4,4'-dicarboxylate and derivatives thereof. In a preferred embodiment, the organic ligand ($L^{-x}$) of the organic ligand salt is at least one selected from the group consisting of imidazolate, pyrimidine-azolate, triazolate, tetrazolate and derivatives thereof. Additional suitable exemplary ligands include, but are not limited to, bidentate carboxylics (i.e. oxalic acid, malonic acid, succinic acid, glutaric acid, phthalic acid, isophthalic acid, terephthalic acid), tridentate carboxylates (i.e. citric acid, trimesic acid), azoles (i.e. 1,2,3-triazole, pyrrodiazole), squaric acid and mixtures thereof.

In preferred embodiments, the metal ($M^{+y}$) of the metal precursor is at least one transition metal selected from the group consisting of Mg, V, Cr, Mo, Zr, Hf, Mn, Fe, Co, Cu, Ni, Zn, Ru, Al, and Ga. As used herein, "metal ion" is selected from the group consisting of elements of groups Ia, IIa, IIIa, IVa to VIIIa and IB to VIb of the periodic table of the elements. In certain other embodiments, the metal precursor may comprise clusters of metal oxides.

In a preferred embodiment, the metal organic framework is at least one selected from the group consisting of MIL-101, MIL-100, MIL-53, MOF-74, UiO-66, UiO-67, ZIF-8, ZIFs, HKUST-1, $M_2$(dobpdc), NU-1000, PCN-222, PCN-224, and derivatives thereof. As used herein, a metal organic framework may refer to compounds consisting of metal ions or clusters coordinated to organic ligands to form one-, two- or three-dimensional structures, with the special feature of porosity. More formally, a metal organic framework is a coordination network with organic ligands containing potential voids. In a preferred embodiment, the nano-crystalline MOF has a percent porosity of greater than 10%, preferably greater than 20%, preferably greater than 25%, preferably greater than 30%, preferably greater than 35%, preferably greater than 40%. MOFs are composed of two major components: a metal ion or cluster of metal ions and an organic molecule often termed a linker. The organic units are typically mono-, di-, tri-, or tetravalent ligands. The choice of metal and linker will dictate the structure and hence properties of the MOF. For example, the metal's coordination preference influences the size and shape of pores by dictating how many ligands can bind to the metal and in which orientation.

In a preferred embodiment, the hybrid material has a weight percentage of the metal organic framework in the range of 5-50% relative to the total weight of the hybrid material, preferably 15-45%, preferably 25-40%, preferably 30-35%, or at least 20%, preferably at least 25%, preferably at least 30%, preferably at least 35%, preferably at least 40%, preferably at least 45%.

In a preferred embodiment, the mesoporous material (MPM) comprises mesopores with an average diameter in the range of 2-50 nm, preferably 4-45 nm, preferably 6-40 nm and micropores with an average diameter in the range of 0.5-5.0 nm, preferably 1.0-4.5 nm, preferably 2.0-4.0 nm. In a preferred embodiment, the mesopores, the micropores, or both are monodisperse having a coefficient of variation of less than 10%, preferably less than 8%, preferably less than 6%, preferably less than 5%, preferably less than 4%, preferably less than 3%. In a preferred embodiment, the hybrid material has a percent porosity of greater than 10%, preferably greater than 20%, preferably greater than 25%, preferably greater than 30%, preferably greater than 35%, preferably greater than 40%. In a preferred embodiment, the hybrid material has a reduced mesoporosity relative to the bare mesoporous material and an increased microporosity relative to the bare mesoporous material.

In a preferred embodiment, the confined metallic nanocrystal has an average longest linear dimension of less than 10 nm, preferably less than 8 nm, preferably less than 5 nm, preferably less than 2.5 nm.

In a preferred embodiment, the MPM has a surface area in the range of 100-1200 $m^2$/g, preferably 200-1100 $m^2$/g, preferably 300-1000 $m^2$/g, preferably 400-900 $m^2$/g, preferably 500-950 $m^2$/g, preferably 600-900 $m^2$/g, preferably 700-850 m²/g, or at least 400 m²/g, preferably at least 600 m²/g, preferably at least 800 m²/g, preferably at least 1000 m²/g.

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or there below. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

As used herein, the verb "comprise" as is used in this description and in the claims and its conjugations are used in its non-limiting sense to mean that items following the word are included, but items not specifically mentioned are not excluded.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure. All references cited herein are incorporated by reference in their entirety.

The following Examples further illustrate the disclosure and are not intended to limit the scope. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

6. EXAMPLES

6.1. Materials and Methods

Chemicals. All chemicals were used as received from Sigma-Aldrich without further purification. $Cr(NO_3)_3 \cdot 9H_2O$, $CrCl_3 \cdot 6H_2O$, $Al(NO_3)_3 \cdot 9H_2O$, $AlCl_3 \cdot xH_2O$, $Co(NO_3)_2 \cdot 6H_2O$, $Ni(NO_3)_2 \cdot 6H_2O$, $ZrOCl_2 \cdot 8H_2O$, $RuCl_3 \cdot xH_2O$, $Zn(NO_3)_3 \cdot 9H_2O$, 1,4-benzenedicarboxylic acid ($H_2BDC$), 1,3,5-benzenetricarboxylic acid ($H_3BTC$), 2-aminoterephthalic acid ($H_2BDC(NH_2)$), monosodium 2-sulfoterephthalate ($H_2BDC(SO_3Na)$), 2,5-dihydroxyterephthalic acid ($H_4DOBDC$), 2,2'-Bipyridine-5,5'-dicarboxylic acid ($H_2BpyDC$), 2-methylimidazol (HMeIM), tetrakis (4-carboxy-phenyl)-porphyrin ($H_4TCPP$). 1,3,6,8-tetrakis (p-benzoic acid)pyrene ($H_4TBAPy$) was synthesized according to the published procedure. See Deria, P.; Bury, W.; Hupp, J. T.; Farha, O. K.: Versatile functionalization of the NU-1000 platform by solvent-assisted ligand incorporation. *Chem. Commun.* 2014, 50, 1965-1968. Triethylamine (TEA), N,N-dimethylformamide (DMF), tetrahydrofuran (THF) and methanol (MeOH) were of analytical grade (Sigma-Aldrich).

Mesoporous materials. Silica(A) [75-250 µm], Silica(B) [200-500 µm], Silica(C) [75-200 µm] and Silica(D) [75-150 µm] were kindly supplied by our commercial partner. SBA-15 was prepared according to the published procedure. Zhao, D. Y.; Feng, J. L.; Huo, Q. S.; Melosh, N.; Fredrickson, G. H.; Chmelka, B. F.; Stucky, G. D.: Triblock copolymer syntheses of mesoporous silica with periodic 50 to 300 angstrom pores. *Science* 1998, 279, 548-552. MCM-41 was provided by Claytec (East Lansing, Mich.), $\gamma$-$Al_2O_3$ by Sasol (Houston, Tex.), $TiO_2$ by Sachtleben (Hausach, Germany) and $ZrO_2$ by Mel Chemicals (Manchester, UK). Mesoporous carbon and HayeSep A (Supelco) [100-120 µm] were supplied by Sigma-Aldrich. All mesoporous materials were degassed at 120° C. overnight under vacuum to remove the adsorbed water.

Ligand salt precursors. $Na_2BDC$ and $Na_3BTC$ ligand salt precursors were prepared from their acid form in water with the stoichiometric amount of NaOH necessary to deprotonate the carboxylic acid of the organic linker followed by a purification step via precipitation in acetone. Alternatively, ligand salt precursor solutions for $H_2BDC(NH_2)$, $H_2BpyDC$, $H_4TCPP$ and $H_4TBAPy$ were directly prepared with the stoichiometric amount of TEA, thereby skipping the step of isolating the ligand salt. $H_2BDC(SO_3Na)$ and HMeIM were directly dissolved in water. $H_4DOBDC$ was dissolved in hot THF due to the insolubility in water of sodium 2,5-dioxyterephthalate coordination polymers. The use of triethylammonium salts did not give rise the targeted MOF-74 structure.

Bulk-type MOFs. For comparison purposes, the following MOFs were prepared and activated according to the reported literature: (Cr)MIL-101 (Ferey, G.; Mellot-Draznieks, C.; Serre, C.; Millange, F.; Dutour, J.; Surble, S.; Margiolaki, I.: A chromium terephthalate-based solid with unusually large pore volumes and surface area. *Science* 2005, 309, 2040-2042 and Serre, C.; Millange, F.; Thouvenot, C.; Noguès, M.; Marsolier, G.; Louër, D.; Férey, G.: Very Large Breathing Effect in the First Nanoporous Chromium(III)-Based Solids: MIL-53 or CrIII(OH).$\{O_2C-C_6H_4-CO_2\}$ $\{HO_2-C-C_6H_4-CO_2H\} \cdot xH_2Oy$. *J. Am. Chem. Soc.* 2002, 124, 13519-13526), (Cr)MIL-100 (Long, P. P.; Wu, H. W.; Zhao, Q.; Wang, Y. X.; Dong, J. X.; Li, J. P.: Solvent effect on the synthesis of MIL-96(Cr) and MIL-100(Cr). *Microporous Mesoporous Mater.* 2011, 142, 489-493), (Cr)MIL-101 (SO$_3$H) (Juan-Alcaniz, J.; Gielisse, R.; Lago, A. B.; Ramos-Fernan-dez, E. V.; Serra-Crespo, P.; Devic, T.; Guillou, N.; Serre, C.; Kapteijn, F.; Gascon, J.: Towards acid MOFs—catalytic performance of sulfonic acid functionalized architectures. *Catal. Sci. Technol.* 2013, 3, 2311-2318), (Al)MIL-100 (Volkringer, C.; Popov, D.; Loiseau, T.; Férey, G.; Burghammer, M.; Riekel, C.; Haouas, M.; Taulelle, F.: Synthesis, Single-Crystal X-ray Microdiffraction, and NMR Characterizations of the Giant Pore Metal-Organic Framework Aluminum Trimesate MIL-100. *Chem. Mater.* 2009, 21, 5695-5697), (Al)MIL-53(NH2) (Couck, S.; Denayer, J. F. M.; Baron, G. V.; Remy, T.; Gas-con, J.; Kapteijn, F.: An Amine-Functionalized MIL-53 Metal-Organic Framework with Large Separation Power for CO$_2$ and CH$_4$. *J. Am. Chem. Soc.* 2009, 131, 6326-+), (Co, Ni)MOF-74 (Dietzel, P. D. C.; Morita, Y.; Blom, R.; Fjellvåg, H.: An In Situ High-Temperature Single-Crystal Investigation of a Dehydrated Metal-Organic Framework Compound and Field-Induced Magnetization of One-Dimensional Metal-Oxygen Chains. *Angew. Chem., Int. Ed.* 2005, 44, 6354-6358 and Dietzel, P. D. C.; Panella, B.; Hirscher, M.; Blom, R.; Fjell-vag, H.: Hydrogen adsorption in a nickel based coordination polymer with open metal sites in the cylindrical cavities of the desolvated frame-work. *Chem. Commun.* 2006, 959-961), (Zr)UiO-66(H,NH$_2$) (Kandiah, M.; Nilsen, M. H.; Usseglio, S.; Jakobsen, S.; Ols-bye, U.; Tilset, M.; Larabi, C.; Quadrelli, E. A.; Bonino, F.; Lillerud, K. P.: Synthesis and Stability of Tagged UiO-66 Zr-MOFs. *Chem. Ma-ter.* 2010, 22, 6632-6640), (Zr)UiO-67(Bpy) (Fei, H.; Cohen, S. M.: A robust, catalytic metal-organic framework with open 2,2-bipyridine sites. *Chem. Commun.* 2014, 50, 4810-4812), (Ru)HKUST-1 (Kozachuk, O.; Luz, I.; Llabrés i Xamena, F. X.; Noei, H.; Kauer, M.; Albada, H. B.; Bloch, E. D.; Marler, B.; Wang, Y.; Muhler, M.; Fischer, R. A.: Multifunctional, Defect-Engineered Metal-Organic Frameworks with Ruthenium Centers: Sorption and Catalytic Properties. *Angew. Chem., Int. Ed.* 2014, 53, 7058-7062), (Zn)ZIF-8 (Cravillon, J.; Münzer, S.; Lohmeier, S.-J.; Feldhoff, A.; Huber, K.; Wiebcke, M.: Rapid Room-Temperature Synthesis and Characterization of Nanocrystals of a Prototypical Zeolitic Imidazolate Framework. *Chem. Mater.* 2009, 21, 1410-1412), (Zr)PCN-222 (Dawei Feng; Zhi-Yuan Gu; Jian-Rong Li; Hai-Long Jiang; ZhangwenWei; Zhou, H.-C.: Zirconium-Metalloporphyrin PCN-222: Mesoporous Metal-Organic Frameworks with Ultrahigh Stability as Biomimetic Catalysts. *Angew. Chem., Int. Ed.* 2012, 51, 10307-10310), (Zr)NU-1000 (Deria et al. 2014) and Co$_2$(dobpdc) (McDonald et al. Cooperative insertion of CO$_2$ in diamine-appended metal-organic frameworks. *Nature* 2015, 519, 303-+). FTIR spectra of these MOFs was used as reference for MOF/MPM hybrid materials. N$_2$ isotherms and pore distribution for (Cr)MIL-101(SO$_3$H) were included in Figures.

Transmission Electron Microscopy (TEM). Transmission electron microscopy (TEM) experiments were performed in a JEOL JEM-2000FX S/TEM microscope with LaB6 emitter at 200 kV with a 120 µm condenser lens aperture and 80 µm objective lens aperture inserted.

Thermogravimetric Analyzer (TGA). Thermal stability measurements were conducted on a Mettler Toledo thermogravimetric analyzer (TGA) using a 5° C./min step to 1000° C. under an air atmosphere.

N$_2$ sorption isotherms. The samples were analyzed in a Micromeritics ASAP (Accelerated Surface Area and Porosimetry) 2020 System. Samples were weighted into tubes with seal frits and degassed under vacuum (<500 µm Hg) with heating. They were initially heated at 150° C. and held for 4 hours, and finally cooled to room temperature and backfilled with N2. The samples were re-weighted before analysis. The analysis adsorptive was N$_2$ at 77K. A multipoint BET surface area was determined from 6 measurements at relative pressures (P/Po) ranging from 0.050 to 0.300 satisfying the four criteria suggested by Rouquerol. See Gomez-Gualdron, D. A., Moghadam, P. Z., Hupp, J. T., Farha, O. K., Snurr, R. Q.: Application of Consistency Criteria To Calculate BET Areas of Micro- And Mesoporous Metal-Organic Frameworks. *J. Am. Chem. Soc.*, 2016, 138, 215-224. Single point adsorption total pore volume was measured near saturation pressure (Po≈770 mmHg). Adsorption average pore width was also calculated. Pore size distribution plot was determined by BJH method with Halsey thickness curve equation and Faas BJH correction.

FTIR: ATR and DRIFTS cell. ATR absorption spectroscopy measurements were performed in the range of 4000-400 cm−1 with a Perkin Elmer Spectrum 100 FTIR spectrometer. The 'in situ' DRIFTS experiments were carried out in a Praying Mantis cell by injecting a nitrogen flow saturated with water for assisting the vapor-phase crystallization at 120° C.

6.2. Examples of a Single Nanocrystal to Single Nanocatalyst Transformation

As examples of the scope of the approach disclosed herein, single metal and metal oxide nanocrystals have been prepared via controlled transformation procedures by using selected supported MOF nanocrystals on mesoporous silica as precursors. Moreover, bimetallic metal oxide nanocrystals have also been prepared by an additional multistep post-synthesis modification (PSM) of the MOF hybrid precursors carried out before controlled transformation, which includes a gas-phase functionalization (see Table 1 and FIGS. 1 and 2) (Servalli, M.; Ranocchiari, M.; Van Bokhoven, J. A.: Fast and high yield post-synthetic modification of metal-organic frameworks by vapor diffusion. *Chemical Communications* 2012, 48, 1904-1906) followed by a selective metalation (Zhang, X.; LLabrés i Xamena, F. X.; Corma, A.: Gold(III)—Metal Organic Framework Bridges the Gap between Homogeneous and Heterogeneous Gold Catalysts. *Journal of Catalysis* 2009, 265, 155-160).

6.3. Example of the Synthesis Approach: Bimetallic [PdCl—SI—(Zr)UiO-66(NH$_2$)/SBA-15] Precursor for the Catalyst Bimetallic [PdCl—SI—(Zr)UiO-66(NH$_2$)/SBA-15] precursor was prepared via solid-state synthesis by following this general procedure: 1) multi-step incipient wetness impregnation of MOF precursor solutions on SBA-15, 2) treatment at specific conditions, 3) general washing treatment, 4) vapor phase post-synthesis functionalization (solid state), and 5) liquid phase post-synthesis metalation. All bimetallic [M$_2$-Z-(M$_1$)MOF/MPM] precursors can be prepared by the following general procedure (steps 1 to 5) as described previously (Cirujano et al. 2017 and PCT Patent Appn. PCT/US2017/046231). Monometallic [(M$_1$)MOF/MPM] precursors are prepared by following only the three first steps (1-3).

Multi-Step Incipient Wetness Impregnation of MOF Precursor Solution on SBA-15

First, a ligand salt precursor solution (TEA)$_2$BDC(NH$_2$) was prepared by dissolving H$_2$BDC(NH$_2$) (1.5 g) loading and TEA (2.5 mL) in 35 mL of water. Second, 10 g of evacuated SBA-15 (overnight under vacuum at 120° C.) were impregnated with the $(TEA)_2BDC(NH_2)$ solution and then dried at 50° C. under vacuum in a rotavapor for 2 h. Subsequently, the resulting dry intermediate $[(TEA)_2BDC(NH_2)/SBA-15]$ was placed in a fluidized bed reactor where it was first treated with a nitrogen flow saturated with concentrated HCl (37%) for 2 hours at room temperature and eventually purged with a nitrogen flow for 2 h to remove the excess HCl. Afterwards, the metal salt precursor solution, prepared by dissolving 2.5 g of $ZrOCl_2.8H_2O$ in 30 mL of water, was used to impregnate the $[H_2BDC(NH_2)/SBA-15]$ mesoporous silica. The resulting $[ZrOCl_2/H_2BDC(NH_2)/SBA-15]$ solid was finally dried at 50° C. under vacuum in a rotavapor for 2 h. All the impregnation steps were done via incipient wetness impregnation.

Treatment at Specific Conditions

The dry solid intermediate $[ZrOCl_2/H_2BDC(NH_2)/SBA-15]$ together with an additive (15 wt. % of $H_2O$) was placed either in a scintillation vial or Pyrex glass bottle capped with a Teflon tap and heated in an oven at 120° C. for 2 h.

General Washing Procedures

After cooling, the resulting $[(Zr)UiO-66(NH_2)/SBA-15]$ precursor, containing 18.6 wt. % of $(Zr)UiO-66(NH_2)$ nanocrystals, was thoroughly washed with distilled water in a filtration funnel. Subsequently, the material was further washed overnight in a Soxhlet extractor with MeOH. All materials were activated overnight at 120° C. under vacuum.

Vapor-Phase Post-Synthesis Functionalization

The evacuated precursor $[(Zr)UiO-66(NH_2)/SBA-15]$ (1 gram) and a tube containing salicylaldehyde (1 mL) were separately placed into a Schlenk. The Schlenk was subsequently closed under vacuum and heated at 100° C. overnight in an oven. The color of the material shifts from pale yellow to orange upon exposure to the salicylaldehyde vapor, which indicates the formation of the imine covalent bond between the MOF and salicylaldehyde leading to a solid containing salicylideneimine groups (or Schiff base, Z=SI). This material corresponds to the intermediate [SI—(Zr)UiO-66(NH_2)/SBA-15].

Liquid-Phase Post-Synthesis Metalation

The metal cation was chelated to the intermediate material containing the Schiff base [SI—(Zr)UiO-66(NH_2)/SBA-15] by soaking for 2-3 hours at room temperature in a solution containing $PdCl_2(CH_3CN)$ (200 mg) in THF (5 mL). Afterwards the material was washed with MeOH and dried at 80° C. under vacuum to obtain the precursor [PdCl—SI—(Zr)UiO-66(NH_2)/SBA-15] containing 1.7 wt. % of Pd, according to XRF. In the same way, several other metal cations can be incorporated into the Schiff base intermediate [SI—(Zr)UiO-66(NH_2)/SBA-15], such as Au, Pt, Ag, Cu, Ni, . . . See the examples in Table 1.

To prepare additional bimetallic nanocatalysts, the steps are as follows. In a first step, a selective PSM of the free amino groups located at the ligands of numerous MOF structures, such as $(Zr)UiO-66(NH_2)$, $(Al)MIL-53 (NH_2)$, $(Ti)MIL-125(NH_2)$, $(Zn)IRMOF-3(NH_2)$, $(V)MIL-101(NH_2)$, $(Fe)MIL-53(NH_2)$, among others, have been functionalized via gas phase treatment with salicylaldehyde vapor at 110° C. to fully convert amino groups into Schiff-base ligands (salicyclidene-imine, SI) (see FIG. 1 and FIG. 2). FIG. 5 shows FTIR characterization of the conversion of amino groups into Schiff-base ligands (SI) during subsequent steps of the synthesis. Subsequently, numerous metal cations have been selectively chelated to the resulting Schiff base by soaking the solid material in a solution containing a metal salt, such as Pd, Pt, Au, Cu, Ni, Mo, Ir, Rh, among others. The faster functionalization rates observed for MOF hybrids compared to bulk MOFs is mainly due to the smaller particle size, excellent dispersion of the MOF nanocrystals within mesoporous silicas, and concentration of MOF nanocrystal on the surface of the support. For instance, lower functionalization rates have been observed for SBA-15 with 9 nm monodimensional channels than for Silica A, which is a mesoporous silica exhibiting tridimensional 30 nm non-regular cavities. Therefore, our novel approach will give rise to a well-defined, structured catalyst upon transformation by selecting the proper metal oxide on the MOF cluster (Mi=Zr, Al, Ti, Zn, V, Fe, . . . ) and incorporating another selected metal at the SI ($M_2$=Pd, Pt, Cu, Ni, Co, Mo, Au, . . . ). The morphology and composition of the resulting nanocatalysts will depend on the transformation treatment and the mesopore dimensionality of the selected silica.

6.3.1. Example of Controlled Transformation: Pyrolysis under Nitrogen or Other Inert Gas Metallic nanocrystals are obtained when the transformation is carried out under nitrogen or other inert gas for temperatures ranging from 300 to 1000° C. In some embodiments, this treatment transforms the organic composition of MOF nanocrystals into carbonaceous species. Nevertheless, TGA and elemental analysis data reveals the complete 'de-carbonization' of MOF nanocrystals leading to carbon- or graphene-free bimetallic nanocatalysts takes place for temperatures of pyrolysis above 600-700° C. This is in contrast to the bulk MOF (above 100 nm) (see FIG. 5 TGA FTIR comparison), in which microporous carbonaceous structures are remaining upon treatment. See Tang, J.; Salunkhe, R. R.; Zhang, H.; Malgras, V.; Ahamad, T.; Alshehri, S. M.; Kobayashi, N.; Tominaka, S.; Ide, Y.; Kim, J. H.; Yamauchi, Y.: Bimetallic Metal-Organic Frameworks for Controlled Catalytic Graphitization of Nanoporous Carbons. *Scientific Reports* 2016, 6, 30295; Masoomi, M. Y.; Morsali, A.: Applications of metal-organic coordination polymers as precursors for preparation of nano-materials. *Coordination Chemistry Reviews* 2012, 256, 2921-2943; Wezendonk, T. A.; Santos, V. P.; Nasalevich, M. A.; Warringa, Q. S. E.; Dugulan, A. I.; Chojecki, A.; Koeken, A. C. J.; Ruitenbeek, M.; Meima, G.; Islam, H. U.; Sankar, G.; Makkee, M.; Kapteijn, F.; Gascon, J.: Elucidating the Nature of Fe Species during Pyrolysis of the Fe-BTC MOF into Highly Active and Stable Fischer-Tropsch Catalysts. *ACS Catalysis* 2016, 6, 3236-3247. Lower temperature pyrolysis (<500° C.) may be used to avoid the carbon release from the nanocatalysts. FIG. 4a shows STEM images of the nanocatalyst prepared by heating in an inert atmosphere.

6.3.2. Example of Controlled Transformation: Calcination of an Oxygen Containing Atmosphere All organic composition is released at lower temperatures when oxygen is used for the transformation treatment. Carbon-free bimetallic nanocatalysts are obtained for temperatures above 300-600° C. FIG. 4b shows STEM images of the nanocatalyst prepared by calcination in an oxygen containing atmosphere.

6.3.3. Example of Controlled Transformation: Reduction with a Hydrogen Containing Atmosphere When a hydrogen containing atmosphere is used, controlled transformation occurs at milder temperatures (from room temperature to 300° C.). Under these conditions, the MOF carbon microstructure is not completely decomposed, although the transition metal cations decorating the MOF nanocrystal are reduced to form a monometallic nanocrystal confined within the microporous cavities of the MOF. Formation of subnanometric metal nanocrystals are confined within the microporous MOF. FIG. 4c shows STEM images of the nanocatalyst prepared by reduction in a hydrogen containing atmosphere.

6.4. Examples of the Scope of the Disclosure

Some examples of supported nanocrystals prepared via our novel approach are shown in Table 1. The selection of these materials does not limit the preparation of other structures.

TABLE 1

Example of mono metallic and bimetallic catalysts prepared via 'single crystals to single nanocatalysts' approach.

| MOF precursor | Treatment | MPM | $M_1$ | $M_2$ | Formula |
|---|---|---|---|---|---|
| Ru-HKUST-1 | $N_2$, 900° C. | S150A | Ru | — | Ru/S150A |
| (Co)MOF-74 | $N_2$, 750° C. | SBA-15 | Co | — | Co/SBA-15 |
| (Ni)MOF-74 | $N_2$, 750° C. | SBA-15 | Ni | — | Ni/SBA-15 |
| (Zr)UiO—66($NH_2$) | $N_2$, 900° C. | S150A | Zr | — | $ZrO_2$/S150A |
| (Fe)MIL-100 | $N_2$, 500° C. | S150A | Fe | — | FeC/S150A |
| (Fe)MIL-100 | $O_2$, 500° C. | S150A | Fe | — | $Fe_3O_4$/S150A |
| (V)MIL-101($NH_2$) | $N_2$, 900° C. | S150A | V | — | $VO_x$/S150A |
| $PdCl_2$—SI—(Zr)UiO—66($NH_2$) | $O_2$, 500° C. | SBA-15 | Zr | Pd | $PdZrO_2$/S150A |
| $PdCl_2$—SI—(Zr)UiO—66($NH_2$) | $N_2$, 900° C. | SBA-15 | Zr | Pd | $PdZrO_2$/SBA-15 |
| $PdCl_2$—SI—(Zr)UiO—66($NH_2$) | $H_2$, 200° C. | SBA-15 | Zr | Pd | Pd/(Zr)UiO—66($NH_2$)/SBA-15 |
| $RuCl_2$—SI—(Zr)UiO—66($NH_2$) | $N_2$, 900° C. | S150A | Zr | Ru | $RuZrO_2$/S150A |
| $IrCl_2$—SI—(Zr)UiO—66($NH_2$)* | $N_2$, 900° C. | S150A | Zr | Ir | $IrZrO_2$/S150A |
| $RhCl_2$—SI—(Zr)UiO—66($NH_2$) | $N_2$, 900° C. | S150A | Zr | Rh | $RhZrO_2$/S150A |
| $PdCl_2$—SI—(Al)MIL-53($NH_2$) | $N_2$, 900° C. | S150A | Al | Pd | $PdAl_2O_3$/S150A |
| $AuCl_2$—SI—(Ti)MIL-125($NH_2$) | $N_2$, 650° C. | S150A | Ti | Au | $RuTiO_2$/S150A |

6.5. Example of Application: Advanced Ammonia Synthesis

Experiments demonstrating the application of the invention to ammonia synthesis are described below. Ru/SiO$_2$ was synthesized with good yield, providing material for testing in a 2-gram fixed-bed micro-reactor. Before being converted into nanocatalysts, the structure of Ru-HKUST-1 was confirmed by matching X-ray Diffraction (XRD), Fourier Transformed Infrared Spectroscopy (FTIR), and BET surface area measurement showing increase in surface area of the silica composite correlated to the presence of MOF. Ru-HKUST-1 was then converted into ruthenium nanoparticles using a 900° C. heat treatment with a slow temperature ramp. At temperatures above 400° C., the high surface area and long-range structure of the MOF breaks down as certain components of the organic linker are gasified and released as $CO_2$. Monoatomic ruthenium is released from complexation and deposited on the surface among the residual organic fragments. Ruthenium atom agglomeration occurs at high temperature, and small, well-dispersed, ruthenium nanoparticles are formed on the surface of the support. A promotion procedure was followed from the literature using barium and cesium nitrates, which have been shown to promote ammonia synthesis with ruthenium catalysts (Bielawa, H.; Hinrichsen, O.; Birkner, A.; Muhler, M.: The ammonia-synthesis catalyst of the next generation: Barium-promoted oxide-supported ruthenium. *Angewandte Chemie—International Edition* 2001, 40, 1061-1063). The promotion was accomplished by wet deposition of barium and cesium nitrate salts from aqueous solutions onto the surface of Ru/SiO$_2$, resulting in the barium- and cesium-promoted Ru/SiO$_2$ catalyst.

Testing of heat-treated Ru/SiO$_2$ catalyst was conducted to gauge activity as compared with a conventional magnetite catalyst used commercially. The catalyst was loaded into a packed bed micro-reactor and following in-situ reduction over a 2-day period, hydrogen and nitrogen were introduced into the reactor at 90 bar total pressure at a gas hourly space velocity (GHSV) of 15,000 h$^{-1}$. The temperature of the reactor was 470° C. The catalyst was tested for 4 hours after reduction. The catalyst showed an average ammonia production rate of 4.59 $g_{NH3}/g_{metal}/h$.

TABLE 2

Comparison of Ru/SiO$_2$ and commercial catalyst characteristics and performance toward ammonia production

| Material | Surface Area (m$^2$/g) | % Ru | % Cs | % Ba | % Si | NH$_3$ production ($g_{NH3}/g_{metal}/h$) |
|---|---|---|---|---|---|---|
| Ru/SiO$_2$ | 188.5 | 3.7 | 27.7 | 8.9 | 25.9 | 4.59 |
| Commercial magnetite | N/A | N/A | N/A | N/A | N/A | 1.06 |

6.6. Example of Application: Liquid Organic Hydrogen Carriers

To illustrate an example of the wide application of the resulting catalysts by taking advantage of their unique features, they are used for a catalytically active platform for a pioneer concept, Fluidized-Nanoreactor Hydrogen Carriers (herein FNHCs), which consists on within fluidized mesoporous silica (herein, Fluidized-Nanoreactors, FN).

OHCs consist on the chemical hydrogen storage by binding $H_2$ to hydrogen-lean molecules by catalytic hydrogenation reactions, which can release via catalytic dehydrogenation. The bound-$H_2$ may be used as fuel for several applications, ranging from realistic 'off-board' hydrogen filling stations to futuristic 'on-board' hydrogen generation on mobile platforms, such as in cars or space ships (Preuster, P.; Papp, C.; Wasserscheid, P.: Liquid Organic Hydrogen Carriers (LOHCs): Toward a Hydrogen-free Hydrogen Economy. *Accounts of Chemical Research* 2017, 50, 74-85.)

In order to evaluate this cncept, 33 wt. % of N-ethylcarbazole (C) was impregnated on 1.7 wt. % $Pd/ZrO_2/SiO_2$ prepared from $PdCl/SI/UiO-66(NH_2)/SiO_2$ treated at 900° C. under nitrogen. The resulting hydrogen-lean FNHC ($H_0$—FNHC) was loaded into a Parr bomb reactor and pressurized to 800 psig with $H_2$ at room temperature. The reactor was heated up to 220° C. and hold until the pressure decreased and subsequently stabilized, thus indicating the end of the hydrogenation step (see FIG. 6). An aliquot (5 mg) of hydrogen-loaded FNHC ($H_x$—FNHC) was analyzed by extracting the $H_2$-loaded N-ethyl carbazole ($H_x$—C) with $CHCl_3$ and analyzed on a GC. Complete hydrogenation of $H_0$—C to $H_x$—C containing 93.0% of $H_{12}$—C, 3.6% of $H_6$—C and 3.4% of $H_4$—C, according to GC analysis. In order to prove the reversibility, the $H_x$—FNHC was pressurized at 30 psig of $H_2$ and heated up to 220° C. holding until the pressure increased and was stabilized, which indicates the end of the dehydrogenation step. The analysis of the $H_2$-unload OHC extracted from the FNHC revealed 74.3% of complete dehydrogenated compound ($H_0$—C) blended with remaining 22% of $H_6$—C and 3.7% of $H_{12}$—C.

6.7. Example of Application: Synthetic Liquid Fuels

Fe catalysts were prepared via direct conversion of (Fe) $MIL-100/SiO_2$ by using two different transformation conditions at 500 C, air and nitrogen, to form $Fe_3O_4/SiO_2$ and $FeC/SiO_2$, respectively. These two catalysts were evaluated for thermal transformation of $CO_2$ to fuels using hydrogen. An example of some of the results obtained by these catalysts containing varying loading of Fe at 320° C., 30 bar and GHSV of 4000 $h^{-1}$ are shown in FIGS. 7 and 8. (Wei, J.; Ge, Q.; Yao, R.; Wen, Z.; Fang, C.; Guo, L.; Xu, H.; Sun, J.: Directly converting $CO_2$ into a gasoline fuel. *Nature Communications* 2017, 8, 15174-82.)

7. GENERALIZED STATEMENTS OF THE DISCLOSURE

The following numbered statements provide a general description of the disclosure and are not intended to limit the appended claims.

Statement 1: A method of preparing a confined metallic nanocatalyst within a mesoporous material (MPM) which comprises: (a) impregnating at least one or more organic compound, comprising one or more multidentate ligand(s) $[A_x(L^{-x})]$ capable of forming coordination bonds with at least one metal ion, on the mesoporous material to form a first intermediate $[(A_x(L^{-x})/MPM)]$; (b) exposing the first intermediate $[(A_x(L^{-x})/MPM)]$ to an acid in gas phase to form a second intermediate $[(H_x(L^{-x})/MPM)]$; (c) adding to the second intermediate $[(H_x(L^{-x})/MPM)]$ a solvent solution of one or more metal ions ($M_1^{+y}$, $M_2^{+y}$, $M_3^{+y}$) so as to form coordination bonds with the one or more multidentate ligand(s) forming a metal organic framework (MOF) precursor confined within a mesoporous material [MOF/MPM], and (d) treating the precursor of step (c) [MOF/MPM] under controlled transformation conditions so as to form the metallic nanocatalyst confined within the mesoporous material.

Statement 2: The method of Statement 1, wherein step (d) further comprises step (d)(1) comprising contacting the precursor of step (c) [MOF/MPM] with one or more organic compounds (Z) to make a second multidentate ligand capable of forming coordination bonds [Z/MOF/MPM]; and step (d)(2) adding a solvent solution of one or more additional metal ion to form a modified MOF precursor with additional metals confined within the mesoporous material [MOF/MPM].

Statement 3: The method of Statements 1 or 2, wherein the chelating ligand (Z) in step (d)(1) comprises a metal binding site for complexing a second metal ion.

Statement 4: The method of Statements 1-3, wherein the controlled transformation conditions cause greater than 90% of the carbon in the MOF to be released from the MOF/MPM.

Statement 5: The method of Statements 1-4, wherein the controlled transformation conditions cause 50%±10% of the carbon in the MOF to be released from the MOF/MPM.

Statement 6: The method of Statements 1-5, wherein the treating under controlled transformation conditions is pyrolysis at a temperature of about 300° C. to about 1000° C. in an inert gas atmosphere.

Statement 7: The method of Statements 1-6, wherein the treating under controlled transformation conditions is calcination at a temperature of about 300° C. to about 600° C. in an atmosphere containing oxygen gas.

Statement 8: The method of Statements 1-7, wherein the treating under controlled transformation conditions is reduction with hydrogen at a temperature of about 25° C. to about 300° C.

Statement 9: The method of Statements 1-8, wherein the confined nanocatalyst is monometallic ($M_1$).

Statement 10: The method of Statements 1-8, wherein the confined nanocatalyst is bimetallic ($M_1$+$M_2$).

Statement 11: The method of Statements 1-8, wherein the confined nanocatalyst has 3 or more metals.

Statement 12: The method of Statements 1-11, wherein the confined nanocatalyst within the mesoporous material has a diameter of less than 10 nm.

Statement 13: The method of Statements 1-12, wherein the mesoporous material is a mesoporous metal oxide, a mesoporous silica, a mesoporous carbon, a mesoporous polymer, a mesoporous silicoalumina (zeolite), a mesoporous organosilica, or a mesoporous aluminophosphate.

Statement 14: The method of Statement 12, wherein the mesoporous metal oxide is aluminum oxide, cerium oxide, titanium oxide, zirconium oxide, or magnesium oxide.

Statement 15: The method of Statements 1-13, wherein the mesoporous material has a surface area of about 100 $m^2/g$ to about 1000 $m^2/g$.

Statement 16: The method of Statements 1-15, wherein the metal ions ($M_1^{+y}$, $M_2^{+y}$, $M_3^{+y}$) are selected from the group consisting of Al, Au, Ce, Co, Fe, Jr, Mo, Ni, Pd, Rh, Ru, Ti, V and Zr or combinations thereof.

Statement 17: The method of Statements 1-16, wherein the multidentate ligand for the MOF is selected from the group consisting of, terephthalate, benzene-1,3,5-tricarboxylate, 2,5-dioxibenzene dicarboxylate, biphenyl-4,4'-dicarboxylate, imidazolate, pyrimidine-azolate, triazolate, tetrazolate, derivatives or combinations thereof.

Statement 18: The method of Statements 1-16, wherein the MOF is selected from HKUST-1, $M_2$(dobpdc), MIL-100, MIL-101, MIL-53, MOF-74, NU-1000, PCN-222, PCN-224, UiO-66, UiO-67, ZIF-8, ZIFs, or derivatives thereof.

Statement 19: The method of Statements 1-18, wherein the mesoporous material is selected from the group consisting of, MCM-41, SBA-15, or commercially available silica.

Statement 20: The method of Statements 1-19, wherein the confined nanocatalyst confined within mesoporous material is further reacted with additional organometallic metal complexes or metal salts with polymers, organometallic ligand precursors, nitrogen-containing organic compounds, phosphorous-containing organic compounds, sulfur-containing organic compounds, boron-containing organic compounds, halide salts, organic halides, or metal atoms added via atomic layer deposition or chemical vapor deposition.

Statement 20: A catalyst made by the method of Statements 1-19.

Statement 21: The catalyst of Statement 20, further comprising an added metal promotor.

Statement 22: The use of the catalyst of Statements 20 or 21, to catalyze alkene ammoxidation reactions, alkene epoxidation, ammonia synthesis, carboxylation reactions, $CO_2$ methanation reactions, conversion of $CO_2$ to fuel, direct methanol synthesis from methane, dry-methane reforming, electrocatalytic ammonia oxidation, electrocatalytic oxygen reduction reactions, Fischer-Tropsch synthesis, hydro-/dehydrogenation of liquid organic hydrogen carriers, hydrotreating and hydroprocessing esterification reactions, methanol synthesis from syngas, reverse water-gas shift reactions, or water-gas shift reactions.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world. It is to be understood that, while the disclosure has been described in conjunction with the detailed description, thereof, the foregoing description is intended to illustrate and not limit the scope. Other aspects, advantages, and modifications are within the scope of the claims set forth below. All publications, patents, and patent applications cited in this specification are herein incorporated by reference as if each individual publication or patent application were specifically and individually indicated to be incorporated by reference.

What is claimed is:

1. A method of preparing a confined metallic nanocatalyst within a mesoporous material (MPM) which comprises:
   (a) impregnating at least one or more organic compound(s), comprising one or more multidentate ligand(s) selected from the group consisting of salts of terephthalate, benzene-1,3,5-tricarboxylate, 2,5-dioxibenzene dicarboxylate, biphenyl-4,4'-dicarboxylate, imidazolate, pyrimidine-azolate, triazolate, tetrazolate, and derivatives, thereof, capable of forming coordination bonds with at least one metal ion, on the mesoporous material to form a first intermediate complex in the MPM;
   (b) exposing the first intermediate complex to an acid in gas phase to form a protonated second intermediate;
   (c) adding to the protonated second intermediate complex a solvent solution of one or more metal ions selected from the group consisting of salts of Al, Au, Ce, Co, Fe, Ir, Mo, Ni, Pd, Rh, Ru, Ti, V, and Zr, so as to form coordination bonds with the one or more multidentate ligand(s) so as to produce a metal organic framework (MOF) precursor confined within a mesoporous material [MOF/MPM]; and
   (d) treating the MOF precursor of step (c) [MOF/MPM] under either
      (i) pyrolysis conditions under nitrogen or other inert gas at temperatures ranging from about 300° C. to about 1000° C.;
      (ii) calcining conditions in the presence of oxygen at a temperature ranging from about 300° C. to about 600° C.; or
      (iii) reductive conditions in an atmosphere containing hydrogen at a temperature ranging from about 25° C. to about 300° C.;
   so as to form the confined metallic nanocatalyst within the mesoporous material.

2. The method of claim 1, wherein step (c) further comprises step (c)(1) comprising contacting the MOF precursor of step (c) [MOF/MPM] with one or more organic compounds to make a second multidentate ligand capable of forming coordination bonds [MOF /MPM']; and step (c)(2) adding a solvent solution of one or more additional metal ion to form a modified MOF precursor with one or more additional metals confined within the mesoporous material [MOF/MPM'].

3. The method of claim 2, wherein one or more organic compounds in step (c)(1) comprises a metal binding site for complexing a second metal ion.

4. The method of claim 1, wherein the treating in step (d)(i), (d)(ii), or (d)(iii) causes greater than 90% of the carbon in the MOF to be released from the MOF/MPM.

5. The method of claim 1, wherein the treating in step (d)(i), (d)(ii), or (d)(iii) causes 50%±10% of the carbon in the MOF to be released from the MOF/MPM.

6. The method of claim 1, wherein the treating in step (d) is pyrolysis conditions under nitrogen or other inert as at a temperature of about 300° C. to about 1000° C.

7. The method of claim 1, wherein the treating in step (d) is calcining conditions in the presence of oxygen calcining at a temperature of about 300° C. to about 600° C.

8. The method of claim 1, wherein the treating in step (d) is with reductive conditions in an atmosphere containing hydrogen at a temperature of about 25° C. to about 300° C.

9. The method of claim 1, wherein the confined nanocatalyst is monometallic.

10. The method of claim 1, wherein the confined nanocatalyst is bimetallic.

11. The method of claim 1, wherein the confined nanocatalyst has 3 or more metals.

12. The method of claim 1, wherein the confined nanocatalyst within the mesoporous material has a diameter of less than 10 nm.

13. The method of claim 1, wherein the mesoporous material is a mesoporous metal oxide, a mesoporous silica, a mesoporous carbon, a mesoporous polymer, a mesoporous silicoalumina (zeolite), a mesoporous organosilica, or a mesoporous aluminophosphate.

14. The method of claim 13, wherein the mesoporous metal oxide is aluminum oxide, cerium oxide, titanium oxide, zirconium oxide, or magnesium oxide.

15. The method of claim 13, wherein the mesoporous material is a mesoporous carbon.

16. The method of claim 1, wherein the mesoporous material has a surface area of about 100 $m^2/g$ to about 1000 $m^2/g$.

17. The method of claim 1, wherein the metal ions in step (c) are selected from the group consisting of Al, Co, Fe, Ni, Ru, and Zr or combinations thereof.

18. The method of claim 1, wherein the multidentate ligand for the MOF is selected from the group consisting of, terephthalate, benzene-1,3,5-tricarboxylate, 2,5-dioxibenzene dicarboxylate, biphenyl-4,4'-dicarboxylate, derivatives or combinations thereof.

19. The method of claim 1, wherein the MOF is selected from HKUST-1, $M_2$(dobpdc), MIL-100, MIL-101, MIL-53, MOF-74, NU-1000, PCN-222, PCN-224, UiO-66, UiO-67, ZIF-8, or ZIFs.

20. The method of claim 1, wherein the mesoporous material is selected from the group consisting of, MCM-41, SBA-15, and or mesoporous silica.

21. The method of claim 1, wherein the confined nanocatalyst confined within mesoporous material is further reacted with materials selected from the group consisting of polymers, organometallic ligand precursors, nitrogen-containing organic compounds, phosphorous-containing organic compounds, sulfur-containing organic compounds, boron-containing organic compounds, halide salts, organic halides, and metal atoms added via atomic layer deposition or chemical vapor deposition, under catalytic conditions.

22. A catalyst made by the method of claim 1.

23. The catalyst of claim 22, further comprising an added metal promotor.

24. A method of catalyzing a reaction selected from the group consisting of alkene ammoxidation reactions, alkene epoxidation, ammonia synthesis, carboxylation reactions, $CO_2$ methanation reactions, conversion of $CO_2$ to fuel, direct methanol synthesis from methane, dry-methane reforming, electrocatalytic ammonia oxidation, electrocatalytic oxygen reduction reactions, Fischer-Tropsch synthesis, hydro-/dehydrogenation of liquid organic hydrogen carriers, hydrotreating and hydroprocessing esterification reactions, methanol synthesis from syngas, reverse water-gas shift reactions, and water-gas shift reactions which comprises contacting reactants with the catalyst of claim 22 under catalytic conditions so to selectively convert the reactants to a desired product.

* * * * *

UNITED STATES PATENT AND TRADEMARK OFFICE
CERTIFICATE OF CORRECTION

| | |
|---|---|
| PATENT NO. | : 11,406,971 B2 |
| APPLICATION NO. | : 17/041944 |
| DATED | : August 9, 2022 |
| INVENTOR(S) | : Ignacio Luz Minguez et al. |

It is certified that error appears in the above-identified patent and that said Letters Patent is hereby corrected as shown below:

In the Claims

Claim 6, Column 24, Line 2, delete "is pyrolysis conditions under nitrogen or other inert as at a" and insert -- is pyrolysis conditions under nitrogen or other inert gas at a --

Claim 7, Column 24, Line 2, delete "is calcining conditions in the presence of oxygen calcining" and insert -- is calcining conditions in the presence of oxygen --

Signed and Sealed this
Twentieth Day of December, 2022

Katherine Kelly Vidal
*Director of the United States Patent and Trademark Office*